(12) United States Patent
Shin et al.

(10) Patent No.: US 9,814,669 B2
(45) Date of Patent: *Nov. 14, 2017

(54) HAIR COSMETIC COMPOSITION CONTAINING LATEX POLYMERS AND A SILICONE-ORGANIC POLYMER COMPOUND

(71) Applicant: L'OREAL, Paris (FR)

(72) Inventors: Christine Shin, East Brunswick, NJ (US); Alisa Victoria Vasilenko, Warminster, PA (US); Aziza Suleiman, Paterson, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/577,740

(22) Filed: Dec. 19, 2014

(65) Prior Publication Data

US 2016/0175237 A1    Jun. 23, 2016

(51) Int. Cl.
 A61Q 5/06 (2006.01)
 A61K 8/895 (2006.01)
 A61K 8/87 (2006.01)
 A61K 8/81 (2006.01)

(52) U.S. Cl.
 CPC ............ *A61K 8/895* (2013.01); *A61K 8/8147* (2013.01); *A61K 8/87* (2013.01); *A61Q 5/06* (2013.01)

(58) Field of Classification Search
 None
 See application file for complete search history.

(56) References Cited

U.S. PATENT DOCUMENTS

| | | | |
|---|---|---|---|
| 3,110,695 A | 11/1963 | Ceresa | |
| 3,304,273 A | 2/1967 | Stamberger | |
| 3,383,351 A | 5/1968 | Paul | |
| 3,412,054 A | 11/1968 | Milligan et al. | |
| 3,523,095 A | 8/1970 | James et al. | |
| 3,915,921 A | 10/1975 | Schlatzer, Jr. | |
| 4,003,699 A | 1/1977 | Rose et al. | |
| RE30,199 E | 1/1980 | Rose et al. | |
| 4,509,949 A | 4/1985 | Huang et al. | |
| 4,644,030 A | 2/1987 | Loewrigkeit et al. | |
| 4,710,374 A | 12/1987 | Grollier et al. | |
| 4,798,721 A | 1/1989 | Yahagi et al. | |
| 4,985,239 A | 1/1991 | Yahagi et al. | |
| 5,061,289 A | 10/1991 | Clausen et al. | |
| 5,085,859 A | 2/1992 | Halloran et al. | |
| 5,156,911 A | 10/1992 | Stewart | |
| 5,173,526 A | 12/1992 | Vijayendran et al. | |
| 5,221,534 A | 6/1993 | DesLauriers et al. | |
| 5,380,340 A | 1/1995 | Neunhoeffer et al. | |
| 5,441,728 A | 8/1995 | Tsaur et al. | |
| 5,534,267 A | 7/1996 | Neunhoeffer et al. | |
| 5,565,216 A | 10/1996 | Cowsar et al. | |
| 5,618,523 A | 4/1997 | Zysman et al. | |
| 5,637,291 A | 6/1997 | Bara et al. |
| 5,663,366 A | 9/1997 | Neunhoeffer et al. |
| 5,679,327 A | 10/1997 | Darkwa et al. |
| 5,708,151 A | 1/1998 | Moeckli |
| 5,753,215 A | 5/1998 | Mougin et al. |
| 5,766,576 A | 6/1998 | Lowe et al. |
| 5,932,194 A | 8/1999 | Plessix et al. |
| 6,013,682 A | 1/2000 | Dalle et al. |
| 6,099,592 A | 8/2000 | Vidal et al. |
| 6,110,451 A | 8/2000 | Matz et al. |
| 6,120,778 A | 9/2000 | Simonnet |
| 6,126,929 A | 10/2000 | Mougin |
| 6,126,948 A | 10/2000 | Simonnet et al. |
| 6,165,446 A | 12/2000 | Samain et al. |
| 6,214,328 B1 | 4/2001 | Chang et al. |
| 6,268,431 B1 | 7/2001 | Snyder et al. |
| 6,284,003 B1 | 9/2001 | Rose et al. |
| 6,338,741 B1 | 1/2002 | Vidal et al. |
| 6,399,050 B1 | 6/2002 | Pasquet et al. |
| 6,464,990 B2 | 10/2002 | Simonnet et al. |
| 6,482,394 B1 | 11/2002 | Schehlmann et al. |
| 6,585,965 B1 | 7/2003 | Carballada et al. |
| 6,592,633 B2 | 7/2003 | Lang et al. |
| 6,613,315 B1 | 9/2003 | Dupuis |
| 6,645,258 B2 | 11/2003 | Vidal et al. |
| 6,703,028 B1 | 3/2004 | Samain et al. |

(Continued)

FOREIGN PATENT DOCUMENTS

| | | |
|---|---|---|
| DE | 2359399 A1 | 6/1975 |
| DE | 3843892 A1 | 6/1990 |

(Continued)

OTHER PUBLICATIONS

Co-pending U.S. Appl. No. 14/576,639, Siliu Tan et al., "Hair Styling Compositions Comprising Latex Polymers," filed Dec. 19, 2014.
Co-pending U.S. Appl. No. 14/578,074, Siliu Tan et al., "Compositions and Methods for Hair," filed Dec. 19, 2014.
Co-pending U.S. Appl. No. 14/577,809, Mark Benn, "Hair Coloring Compositions Comprising Latex Polymers," filed Dec. 19, 2014.
Co-pending U.S. Appl. No. 14/577,579, Siliu Tan et al., "Hair Styling Compositions Comprising Latex Polymers and Wax Dispersions," filed Dec. 19, 2014.
Co-pending U.S. Appl. No. 14/586,105, Siliu Tan et al., "Compositions and Methods for Hair," filed Dec. 30, 2014.
Co-pending U.S. Appl. No. 14/578,122, Christine Shin, "Hair Cosmetic Composition Containing a Polyurethane Latex Polymer and a Silicone Organic Polymer Compound," filed Dec. 19, 2014.
Co-pending U.S. Appl. No. 13/931,329; Siliu Tan et al., "Compositions and Methods for Treating Hair," filed Jun. 28, 2013.
Co-pending U.S. Appl. No. 13/931,187; Siliu Tan et al., "Compositions and Methods for Treating Hair," filed Jun. 28, 2013.
Co-pending U.S. Appl. No. 13/931,204; Siliu Tan et al., "Compositions and Methods for Treating Hair," filed Jun. 28, 2013.

(Continued)

*Primary Examiner* — Jyothsna Venkat
(74) *Attorney, Agent, or Firm* — The Marbury Law Group, PLLC

(57) ABSTRACT

Disclosed are hair cosmetic compositions comprising at least two latex polymers selected from acrylate latex polymers and polyurethane latex polymers, wherein at least one latex polymer is a film-forming polymer, and at least one silicone-organic polymer compound. Methods of imparting durable styling or shaping benefits and/or frizz control to hair by applying the hair cosmetic compositions onto hair are also disclosed.

16 Claims, No Drawings

(56) References Cited

U.S. PATENT DOCUMENTS

| | | |
|---|---|---|
| 6,726,916 B1 | 4/2004 | Ramin |
| 6,730,789 B1 | 5/2004 | Birault et al. |
| 6,946,123 B2 | 9/2005 | De La Poterie et al. |
| 7,211,244 B2 | 5/2007 | Auguste et |
| 7,651,693 B2 | 1/2010 | Merlau et al. |
| 7,740,832 B1 | 6/2010 | Rollat-Corvol et al. |
| 7,785,613 B2 | 8/2010 | Collin et al. |
| 7,993,632 B2 | 8/2011 | Lezer et al. |
| 8,343,238 B1 | 1/2013 | Lopez et al. |
| 8,398,961 B2 | 3/2013 | Kaplan et al. |
| 8,691,200 B2 | 4/2014 | Vilbert |
| 8,865,147 B2 | 10/2014 | Rizk et al. |
| 2002/0007521 A1 | 1/2002 | Lang et al. |
| 2002/0010970 A1 | 1/2002 | Cottard et al. |
| 2002/0022009 A1 | 2/2002 | De La Poterie et al. |
| 2002/0050013 A1 | 5/2002 | Vidal et al. |
| 2002/0055562 A1 | 5/2002 | Butuc |
| 2002/0198328 A1 | 12/2002 | L'Alloret |
| 2003/0019051 A9 | 1/2003 | Vidal et al. |
| 2003/0026815 A1 | 2/2003 | Scott et al. |
| 2003/0044440 A1 | 3/2003 | Toumi |
| 2003/0053976 A1 | 3/2003 | Tournilhac et al. |
| 2003/0059377 A1 | 3/2003 | Riley |
| 2003/0059388 A1 | 3/2003 | Auguste et al. |
| 2003/0064045 A1 | 4/2003 | Tournilhac et al. |
| 2003/0103927 A1 | 6/2003 | Maubru |
| 2003/0138465 A9 | 7/2003 | Douin et al. |
| 2003/0147832 A1 | 8/2003 | L'Alloret |
| 2003/0161804 A1 | 8/2003 | Perron et al. |
| 2004/0071646 A1 | 4/2004 | Pataut et al. |
| 2004/0096474 A1 | 5/2004 | Merlau et al. |
| 2004/0214913 A1 | 10/2004 | L'Alloret |
| 2005/0008605 A1 | 1/2005 | L'Alloret |
| 2005/0020779 A1 | 1/2005 | Mougin et al. |
| 2005/0025736 A1 | 2/2005 | Jachowicz et al. |
| 2005/0048016 A1 | 3/2005 | Lebreton et al. |
| 2005/0053568 A1 | 3/2005 | Aubrun-Sonneville et al. |
| 2005/0065253 A1 | 3/2005 | Collin et al. |
| 2005/0089490 A1 | 4/2005 | Jachowicz et al. |
| 2006/0115446 A1 | 6/2006 | Rollat-Corvol et al. |
| 2006/0134043 A1 | 6/2006 | Nakamura |
| 2006/0182702 A1 | 8/2006 | Lazzeri et al. |
| 2006/0292095 A1 | 12/2006 | Biatry et al. |
| 2007/0031361 A1 | 2/2007 | Herrmann et al. |
| 2007/0190008 A1 | 8/2007 | Campain et al. |
| 2007/0224140 A1 | 9/2007 | Quadir et al. |
| 2007/0286833 A1 | 12/2007 | Keller et al. |
| 2008/0138307 A1 | 6/2008 | Bazemore et al. |
| 2008/0175808 A1 | 7/2008 | Pavel |
| 2008/0305064 A1 | 12/2008 | Bui et al. |
| 2009/0035335 A1 | 2/2009 | Marotta et al. |
| 2009/0060858 A1 | 3/2009 | Schwarzwaelder et al. |
| 2009/0074695 A1 | 3/2009 | Mahe et al. |
| 2009/0280076 A1 | 11/2009 | Yoshida et al. |
| 2009/0297467 A1 | 12/2009 | Laurent et al. |
| 2009/0317432 A1 | 12/2009 | Kergosien |
| 2010/0028284 A1 | 2/2010 | Atis et al. |
| 2010/0119467 A1 | 5/2010 | Dumousseaux et al. |
| 2010/0189678 A1 | 7/2010 | Knappe et al. |
| 2010/0278770 A1 | 11/2010 | Arditty et al. |
| 2011/0014139 A1 | 1/2011 | Viala et al. |
| 2011/0015279 A1 | 1/2011 | Doerr et al. |
| 2011/0097289 A1 | 4/2011 | Viala et al. |
| 2011/0097293 A1 | 4/2011 | Grey et al. |
| 2011/0150802 A1 | 6/2011 | Bui et al. |
| 2011/0150807 A1* | 6/2011 | Bui ............ A61K 8/044 424/70.7 |
| 2012/0247500 A1 | 10/2012 | Plos et al. |
| 2012/0282309 A1 | 11/2012 | Dihora et al. |
| 2012/0308496 A1 | 12/2012 | Viala et al. |
| 2013/0084256 A1 | 4/2013 | Li et al. |
| 2013/0167863 A1 | 7/2013 | Schmelz et al. |
| 2013/0171084 A1 | 7/2013 | Kawaratani et al. |
| 2013/0284198 A1 | 10/2013 | Rizk et al. |
| 2014/0102468 A1 | 4/2014 | Pistorio et al. |
| 2014/0105845 A1 | 4/2014 | Bui et al. |
| 2014/0105945 A1 | 4/2014 | Bui et al. |
| 2014/0186270 A1 | 7/2014 | Suleiman et al. |
| 2015/0004116 A1* | 1/2015 | Tan ............ A61K 8/87 424/70.13 |
| 2015/0004119 A1 | 1/2015 | Tan et al. |
| 2015/0004120 A1* | 1/2015 | Tan ............ A61K 8/87 424/70.16 |
| 2015/0004121 A1* | 1/2015 | Tan ............ A61K 8/87 424/70.16 |

FOREIGN PATENT DOCUMENTS

| | | |
|---|---|---|
| DE | 4133957 A1 | 4/1993 |
| DE | 19543988 A1 | 5/1997 |
| EP | 0216479 A1 | 4/1987 |
| EP | 0692237 A1 | 1/1996 |
| EP | 0714954 A2 | 6/1996 |
| EP | 0874017 A2 | 10/1998 |
| EP | 0898958 A1 | 3/1999 |
| EP | 1291051 A2 | 3/2003 |
| EP | 1466588 A1 | 10/2004 |
| EP | 1652509 A2 | 5/2006 |
| EP | 2356981 A1 | 8/2011 |
| EP | 2570192 A1 | 3/2013 |
| FR | 2733749 A1 | 11/1996 |
| FR | 2774899 A1 | 8/1999 |
| FR | 2801308 A1 | 5/2001 |
| FR | 2856923 A1 | 1/2005 |
| FR | 2889943 A1 | 3/2007 |
| GB | 1026978 A | 4/1966 |
| GB | 1040452 A | 8/1966 |
| GB | 1153196 A | 5/1969 |
| WO | 9408969 A1 | 4/1994 |
| WO | 9408970 A1 | 4/1994 |
| WO | 9501772 A1 | 1/1995 |
| WO | 9515144 A1 | 6/1995 |
| WO | 9615765 A1 | 5/1996 |
| WO | 0119333 A1 | 3/2001 |
| WO | 2005100444 A1 | 10/2005 |
| WO | 2007/102972 A1 | 9/2007 |
| WO | 2010133658 A2 | 11/2010 |
| WO | 2011056332 A1 | 5/2011 |
| WO | 2011069786 A2 | 6/2011 |
| WO | WO 2011/069786 * | 6/2011 |
| WO | 2011137338 A2 | 11/2011 |
| WO | 2012/072774 A1 | 6/2012 |
| WO | 2013059106 A1 | 4/2013 |
| WO | 2013074210 A1 | 5/2013 |
| WO | 2013092378 A1 | 6/2013 |
| WO | 2013092379 A1 | 6/2013 |
| WO | 2013092380 A1 | 6/2013 |
| WO | 2013092381 A1 | 6/2013 |
| WO | 2013092382 A1 | 6/2013 |
| WO | 2013092562 A1 | 6/2013 |
| WO | 2013092779 A2 | 6/2013 |
| WO | 2013092788 A1 | 6/2013 |
| WO | 2014001390 A1 | 1/2014 |
| WO | 2014001391 A1 | 1/2014 |
| WO | 2014/058856 A1 | 4/2014 |
| WO | 2014/062334 A1 | 4/2014 |
| WO | 2014071354 A1 | 5/2014 |
| WO | 2014124066 A1 | 8/2014 |

OTHER PUBLICATIONS

Co-pending U.S. Appl. No. 13/931,222; Siliu Tan et al., "Compositions and Methods for Treating Hair," filed Jun. 28, 2013.

Co-pending U.S. Appl. No. 13/931,238; Siliu Tan et al., "Compositions and Methods for Treating Hair," filed Jun. 28, 2013.

Co-pending U.S. Appl. No. 13/931,248; Siliu Tan et al., "Compositions and Methods for Treating Hair," filed Jun. 28, 2013.

Co-pending U.S. Appl. No. 13/931,260; Siliu Tan et al., "Compositions and Methods for Treating Hair," filed Jun. 28, 2013.

Co-pending U.S. Appl. No. 13/931,276; Siliu Tan et al., "Compositions and Methods for Treating Hair," filed Jun. 28, 2013.

Co-pending U.S. Appl. No. 13/931,288; Siliu Tan et al., "Compositions and Methods for Treating Hair," filed Jun. 28, 2013.

(56) References Cited

OTHER PUBLICATIONS

Co-pending U.S. Appl. No. 13/931,298; Siliu Tan et al., "Compositions and Methods for Treating Hair," filed Jun. 28, 2013.
Co-pending U.S. Appl. No. 13/931,312; Siliu Tan et al., "Compositions and Methods for Treating Hair," filed Jun. 28, 2013.
English language abstract for EP 0770375 (May 2, 1997).
English language abstract for EP0898960 (Mar. 3, 1999).
English language abstract for EP1082953 (Mar. 14, 2001).
English language abstract for FR2633940 (Jul. 12, 1991).
English language abstract for FR2898050 (Sep. 7, 2007).
English language abstract for FR2968978 (Jun. 22, 2012).
English language Abstract of FR2834458 (Jul. 11, 2003).
Galgoci, Ernest C., et al., "Solvent-Free Urethane-Acrylic Hybrid Polymers for Coatings," JCT Coatings Tech, 2 (13), Feb. 2005, pp. 28-36.
International Search Report for Application No. PCT/US2014/044036, dated Oct. 21, 2014, 3 pages.
International Search Report for Application No. PCT/US2014/044377, dated Oct. 31, 2014, 3 pages.
International Search Report for Application No. PCT/US2014/044557, dated Oct. 13, 2014, 3 pages.
International Search Report for Application No. PCT/US2014/044587, dated Oct. 31, 2014, 3 pages.
International Search Report for Application No. PCT/US2014/044610, dated Oct. 31, 2014, 4 pages.
Jachowicz, J., et al., "Mechanical Analysis of Elasticity and Flexibility of Virgin and Polymer-Treated Hair Fiber Assemblies," J. Cosmet. Sci., 53, Nov./Dec. 2002, pp. 345-361.
Non-Final Office Action for U.S. Appl. No. 13/931,187, dated Feb. 13, 2015.
Non-Final Office Action for U.S. Appl. No. 13/931,204, dated Feb. 20, 2015.
Non-Final Office Action for U.S. Appl. No. 13/931,238, dated Feb. 13, 2015.
Non-Final Office Action for U.S. Appl. No. 13/931,248, dated Feb. 20, 2015.
Non-Final Office Action for U.S. Appl. No. 13/931,260, dated Feb. 20, 2015.
Non-Final Office Action for U.S. Appl. No. 13/931,276, dated Feb. 17, 2015.
Non-Final Office Action for U.S. Appl. No. 13/931,288, dated Feb. 18, 2015.
Non-Final Office Action for U.S. Appl. No. 13/931,298, dated Feb. 20, 2015.
Non-Final Office Action for U.S. Appl. No. 13/931,312, dated Feb. 18, 2015.
Non-Final Office Action for U.S. Appl. No. 13/931,329, dated Feb. 13, 2015.
Polyquats As Conditioning Agents, 2009. Retrieved from the Internet.
English language abstract for DE 102009054516 (Jun. 16, 2011).
English language abstract for EP 0847752 (Jun. 17, 1998).
English language abstract for FR 2961103 (Dec. 16, 2011).
English language abstract for JP H05-163124 (Jun. 29, 1993).
English language abstract for KR 20100105168 (Sep. 29, 2010).
Final Office Action for co-pending U.S. Appl. No. 13/931,187 (Jul. 20, 2015).
Non-Final Office Action for co-pending U.S. Appl. No. 13/931,222 (Apr. 7, 2015).
Final Office Action for co-pending U.S. Appl. No. 13/931,222 (Jul. 28, 2015).
English language abstract for JP H021956 (Jan. 8, 1990).
International Search Report and Written Opinion for counterpart Application PCT/US2015/065967, dated Jul. 5, 2016.
International Search Report and Written Opinion for counterpart Application PCT/US2015/065975, dated Jul. 5, 2016.
International Search Report and Written Opinion for copending Application No. PCT/US2015/066818, dated Feb. 26, 2016.
Extended European Search Report for counterpart EP Application No. 14817057.4, dated Nov. 2, 2016.
Extended European Search Report for counterpart EP Application No. 14818467.4, dated Nov. 9, 2016.
Extended European Search Report for counterpart EP Application No. 14818460.9, dated Nov. 21, 2016.
Extended European Search Report for counterpart EP Application No. 14817786.8, dated Oct. 14, 2016.

\* cited by examiner

HAIR COSMETIC COMPOSITION CONTAINING LATEX POLYMERS AND A SILICONE-ORGANIC POLYMER COMPOUND

FIELD OF THE INVENTION

The present application relates to a shampoo- and/or wash-resistant hair cosmetic composition containing at least two latex polymers and a silicone-organic polymer compound and to a method of imparting durable styling or shaping properties to hair and/or controlling the frizziness of hair using the hair cosmetic composition of the present invention.

BACKGROUND OF THE INVENTION

Consumers of hair cosmetic products such as hair care and hair styling products actively seek out multi-functional, new products that can impart good styling benefits to hair, are durable or last longer on the hair, even with several washings or shampooings and can impart other cosmetic attributes. At the same time, such products have to be pleasing to the senses, both on application and in use, and which have innovative, interesting and/or pleasing textures, preferably without any sacrifice to functional performance. In addition, many consumers seek hair care products which provide a light feel, are easy to apply, moisturize or condition, and add shine to the hair. The resulting feel and texture of the product during the application process, in addition to the feel of the hair after the application, are also important elements of such commodities.

It is also highly desirable for manufacturers of hair cosmetic products to make products that prevent or minimize the frizziness of hair, particularly under high humidity conditions in which hair tends to absorb moisture causing it to be less manageable, which makes it more difficult to shape and style hair. Applying a coating, such as a moisture barrier or a film on the hair can help to keep moisture out of the hair, allowing for more efficient hair shaping and maintenance of hair shape, even in extreme humidity conditions.

Thus one challenge for manufacturers of hair cosmetic products is in making products that help hair maintain its shape or style even after several washing or shampooings/washings. These products are also expected to impart longer lasting frizz control, as well as prevent or minimize the reversion of curly hair that has been straightened to a curly state, especially under very humid conditions.

Traditional compositions on the cosmetic market appear in various forms. They can range anywhere from solutions, foams, gels, creams, waxes, mousses, sprays, serums, to aerosols and can impart a variety of levels of care and cosmeticity depending on the state of the hair and skin. However, these conventional cosmetic compositions contain emulsifying systems which may have limitations and may be less appealing to the consumer. For example, the use of silicone compounds in some of these compositions to achieve desirable shine or certain textures and feel may result in other limitations. Such limitations may include sticky or greasy products, irritation on the skin/scalp, a heavy or oily feel to the hair and skin, and the use of high levels of raw materials or additional ingredients to correct for the detrimental effects of other ingredients, leading to a costly product. Therefore, there is still a need to improve currently marketed commodities in order to provide the consumer with innovative formulations that present sensory, functionality and cost-effective perspectives on cosmetic products.

Generally, products that are designed to impart styling or shaping benefits may come in the form of hair styling or hair care/hair treatment products. Some drawbacks associated with current products for styling or shaping the hair are that the product is often sticky or tacky and/or often produces a film that imparts a sticky or tacky feel, and styled hair that is stiff and/or "crunchy" (i.e. the film is hard and brittle resulting in a crunching feel or sound when the hair is touched), which is undesirable for most consumers. Also challenges exist with formulating hair care/hair treatment products such as rinse-out products (e.g., shampoos, conditioners, hair masques, hair treatments) that impart long-lasting styling, shaping or anti-frizz benefits to the hair, even after rinsing out the products from hair.

Current products for imparting styling or shaping benefits to the hair typically include water soluble film-forming polymers. Depending on the chemical make-up of these polymers, they may be either soluble in water, or they may be water insoluble polymers which are made water soluble via various chemical modifications, such as neutralization. Solutions comprising these polymers tend to be viscous, i.e. as the concentration of the polymer increases, its viscosity builds up rapidly. Translated to styling applications, as the solvent evaporates, the polymer solution becomes thicker on the hair surface, resulting in a sticky or tacky film. These products also tend to exhibit problems with product spreadability, hair manageability, and low degree of humidity resistance which is particularly a problem in hot and humid countries.

Thus, the ability to maintain the shape of hair, and achieve a strong frizz control, good styling hold, good texture and shine on hair, while providing a clean, natural and light-weight feel to the hair remain as additional areas for improvement, particularly in connection with certain type of polymers such as silicone-based polymers.

It has now been discovered that by providing a composition comprising at least two latex polymers, wherein at least one of said latex polymers is a film-forming polymer, and at least one silicone-organic compound, it is possible to form a film on a substrate such as hair that has certain desirable properties, such as durable or long lasting style and frizz control. It was also discovered that frizz control benefits can be long-lasting, i.e, frizz control was observed even after shampooing and/or washing the hair or even after several shampoo and/or wash cycles and/or in high humidity conditions. It has also been discovered that said composition can impart shape and/or maintain the shape of hair, provide a good styling hold, and good texture and shine to the hair as well as a clean, natural, and/or "invisible" feel, and a lack of stickiness. Such compositions may be useful in hair-styling applications wherein styling benefits such as a natural look, curling or straightening, and styling hold are desired.

Moreover, compositions according to embodiments of the invention may be prepared that deliver a surprisingly broad range of hair styling or shaping benefits, such as, for example, from low to high style-hold and curl elongation or hair straightening properties, for example by varying the weight ratio between both latex polymers, and/or varying the weight ratio of the combined amount of the latex polymers to the silicone-organic polymer compound, with or without additives.

SUMMARY OF THE INVENTION

The present invention is directed to a hair cosmetic composition comprising, in a cosmetically acceptable carrier, at least two latex polymers selected from acrylate latex polymers and polyurethane latex polymers and at least one silicone-organic polymer compound;

wherein at least one latex polymer is a film-forming polymer;
    wherein the at least two latex polymers are selected from:
        (a) polymer A, having a Young's modulus ranging from about 0.1 MPa to about 10 MPa and a strain, under stress at 0.5 MPa, of at least about 1%;
        (b) polymer B, having a Young's modulus ranging from about 10 MPa to about 6 GPa and a strain, under stress at 0.5 MPa, of less than about 5%; and
        (c) polymer C, selected from non-film-forming latex polymers;

wherein the at least two latex polymers are present in a combined amount ranging from about 0.25% to about 3.5% by weight, relative to the weight of the composition;
wherein the at least one silicone-organic polymer compound is present in a total amount ranging from about 0.5% to about 10% by weight, relative to the weight of the composition; and
wherein the at least two latex polymers are present in the composition in a weight ratio ranging from about 10:1 to about 1:10.

The present invention also relates to a method of imparting durable styling or shaping properties and/or long-lasting frizz control to hair, comprising applying the above-described composition to the hair.

The present invention further relates to a method of styling or shaping hair, comprising applying the above-described composition to the hair. Such styling methods may comprise shaping, reshaping, positioning, repositioning, adding volume to, curling, or straightening the hair, in order to achieve a certain hair style or appearance.

It has been surprisingly and unexpectedly discovered that the application of the composition of the present invention onto hair resulted in desirable and beneficial effects on the hair, for example, frizz control, styling and shaping benefits that last even with multiple shampooing and/or washing cycles, as well as manageability of hair, humidity resistance, and hair curl elongation or straightening. Additional advantages can be achieved such as smoothness, softness, and clean/natural and light-weight/non-greasy or non-oily feel.

The compositions of the present invention can be formulated as a spray product containing volatile organic solvents/compounds.

DETAILED DESCRIPTION

As used herein, the expression "at least one" means one or more and thus includes individual components as well as mixtures/combinations.

It is also to be understood that, as used herein the terms "the," "a," or "an," mean "at least one," are understood to encompass the plural as well as the singular and should not be limited to "only one" unless explicitly indicated to the contrary. Thus, for example, the use of "an acid" is intended to mean at least one acid.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

The term "comprising" (and its grammatical variations) as used herein is used in the inclusive sense of "having" or "including" and not in the exclusive sense of "consisting only of".

"Keratin fiber" as used herein, includes, but is not limited to hair, such as hair on the human head and eyelashes.

"Film former" or "film forming polymer" as used herein means a polymer or resin that leaves a film on the substrate to which it is applied, for example, after a solvent accompanying the film former has evaporated, absorbed into and/or dissipated on the substrate. These terms may also refer to a polymer capable, by itself or in the presence of an auxiliary film forming polymer, of forming a continuous or a discontinuous film that adheres to a support and especially to keratin substrates such as keratin fibers or hair.

"Film former" or "film forming polymer" as used herein may also be referred to as fixing polymers when such polymers are employed to fix or keep keratin fibers in a particular configuration or shape or arrangement.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The terms "organic compound" and "having an organic structure" mean compounds containing carbon atoms and hydrogen atoms and optionally heteroatoms such as S, O, N or P, alone or in combination.

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

The term "stable" as used herein means that the composition does not exhibit phase separation and/or crystallization.

As used herein, the terms "applying a composition onto keratin fibers" and "applying a composition onto hair" and variations of these phrases are intended to mean contacting the fibers or hair, with at least one of the compositions of the invention, in any manner.

The term "treat" (and its grammatical variations) as used herein refers to the application of the compositions of the present invention onto keratin fibers such as hair.

The term "style" or styling" as used herein includes shaping, straightening, curling, or placing a keratin fiber such as hair, in a particular arrangement, form or configuration; or altering the curvature of a keratin fiber or other substrate; or repositioning a keratin fiber or other substrate to a different arrangement, form or configuration.

As used herein, the terms "method of styling keratin fibers" or "method of styling hair" is understood to mean any method for modifying the appearance of the keratin fibers or the hair with respect to their spatial arrangement or configuration or curvature or form. When the keratin fibers comprise hair on the human head, the term "method of styling keratin fibers" or "method of styling hair" is also understood to mean any method for curling or waving or embossing the hair or smoothing or straightening the hair, or spiking the hair.

The compositions and methods of the present invention can comprise, consist of, or consist essentially of the essential elements and limitations of the invention described herein, as well as any additional or optional ingredients, components, or limitations described herein or otherwise useful.

Unless otherwise specified herein, all percentages and ratios of components are by weight, relative to the total weight of the final composition.

In an embodiment, the hair cosmetic composition of the present invention contains, in a cosmetically acceptable carrier, at least two latex polymers selected from acrylate latex polymers and polyurethane latex polymers and at least one silicone-organic polymer compound;
  wherein at least one latex polymer is a film-forming polymer;
  wherein the at least two latex polymers are selected from:
  (a) polymer A, having a Young's modulus ranging from about 0.1 MPa to about 10 MPa and a strain, under stress at 0.5 MPa, of at least about 1%;
  (b) polymer B, having a Young's modulus ranging from about 10 MPa to about 6 GPa and a strain, under stress at 0.5 MPa, of less than about 5%; and
  (c) polymer C, selected from non-film-forming latex polymers;
  wherein the at least two latex polymers are present in a combined amount ranging from about from about 0.45 to about 2.21% by weight, relative to the weight of the composition;
  wherein the at least one silicone-organic polymer compound is present in a total amount ranging from about 2% to about 4% by weight, relative to the weight of the composition; and
  wherein the at least two latex polymers are present in the composition in a weight ratio ranging from about 3:1 to about 1:3.

In an embodiment, the hair cosmetic composition of the present invention contains, in a cosmetically acceptable carrier, at least two latex polymers selected from acrylate latex polymers and polyurethane latex polymers and at least one silicone-organic polymer compound;
wherein at least one latex polymer is a film-forming polymer;
wherein the at least two latex polymers are selected from:
  (a) polymer A, having a Young's modulus ranging from about 0.1 MPa to about 10 MPa and a strain, under stress at 0.5 MPa, of at least about 1%; and
  (b) polymer B, having a Young's modulus ranging from about 10 MPa to about 6 GPa and a strain, under stress at 0.5 MPa, of less than about 5%; and
  wherein the at least two latex polymers are present in a combined amount ranging from about 0.375 to about 2.55% by weight, relative to the weight of the composition;
  wherein the at least one silicone-organic polymer compound is present in a total amount ranging from about 1% to about 5% by weight, relative to the weight of the composition; and
  wherein the at least two latex polymers are present in the composition in a weight ratio ranging from about 10:1 to about 1:10.

In another embodiment, the hair cosmetic composition of the present invention contains, in a cosmetically acceptable carrier, two latex polymers selected from acrylate latex polymers and polyurethane latex polymers and at least one silicone-organic polymer compound;
  wherein at least one latex polymer is a film-forming polymer;
  wherein the at least two latex polymers are selected from:
  (a) polymer A, having a Young's modulus ranging from about 0.1 MPa to about 10 MPa and a strain, under stress at 0.5 MPa, of at least about 1%; and
  (b) polymer B, having a Young's modulus ranging from about 10 MPa to about 6 GPa and a strain, under stress at 0.5 MPa, of less than about 5%; and
  wherein the at least two latex polymers are present in a combined amount ranging from about 0.25 to about 3.5% by weight, relative to the weight of the composition;
  wherein the at least one silicone-organic polymer compound is present in a total amount ranging from about 0.5% to about 10% by weight, relative to the weight of the composition;
  wherein the at least two latex polymers are present in the composition in a weight ratio ranging from about 10:1 to about 1:10; and
  wherein polymer A is selected from polyurethane latex polymers and polymer B is selected from acrylate latex polymers.

In an embodiment, the polyurethane latex polymers in the above-described compositions has a Young's modulus ranging from about 0.1 MPa to about 10 MPa, and a strain, under stress at 0.5 MPa, of at least about 1%.

In another embodiment, the acrylate latex polymers in the above-described compositions has a Young's modulus ranging from about 10 MPa to about 6 GPa and a strain, under stress at 0.5 MPa, of less than about 5%.

In other embodiments, the polyurethane latex polymers are selected from polyurethane-34 and the acrylate latex polymers are selected from acrylates copolymer.

In an embodiment, the at least one silicone-organic polymer compound in the above-described compositions is dispersed in an alcoholic medium.

In an embodiment, the at least one silicone-organic polymer compound in the above-described compositions is selected from Crotonic Acid/Vinyl C8-12 Isoalkyl Esters/VA/Bis-Vinyldimethicone Crosspolymer.

In another embodiment, the at least one silicone-organic polymer compound in the above-described compositions is in partially or fully neutralized neutralized form.

In an embodiment, the cosmetically acceptable carrier is selected from water, at least one organic solvent, and mixtures thereof.

In another embodiment, the cosmetically acceptable carrier comprises water, and at least one organic solvent.

In other embodiments, the at least one organic solvent in the above-described compositions is selected from ethanol, isopropyl alcohol, butanol, propylene glycol, butylene glycol, pentylene glycol, hexylene glycol, glycerol, isododecane, mineral oil, polybutene, dipropylene glycol n-butyl ether, and mixtures thereof.

In yet other embodiments, the above-described compositions of the present invention further comprise a propellant.

In certain embodiments, the above-described compositions are hair styling or hair shaping compositions.

In yet other embodiments, the above-described compositions are anti-frizz hair cosmetic compositions.

In an embodiment, the present invention relates to methods of controlling frizziness of hair comprising applying to the hair any one of the above described compositions. Such methods may further comprise the additional step of heating the hair and/or applying a smoothing action to the hair.

In some embodiments, the above-described compositions of the present invention impart frizz control benefits to hair that remain after one or more shampoo and/or wash cycles.

Latex Polymers

According to various exemplary embodiments of the invention, the at least two latex polymers, at least one of which is a film-forming polymer, may be chosen from acrylate latex polymers and polyurethane latex polymers.

In some embodiments, when the first latex polymer is chosen from acrylate latex polymers, the second latex polymer is chosen from polyurethane latex polymers; and when the first latex polymer is chosen from polyurethane latex polymers, the second latex polymer is chosen from acrylate latex polymers.

In various embodiments according to the invention, the at least two latex polymers may be present, on a dry weight basis, in a combined amount ranging from about 0.25 to about 3.5% by weight, preferably from about 0.3 to about 3% by weight, more preferably from about 0.375 to about 2.55% by weight, or even more preferably from about 0.45 to about 2.21% by weight, including all ranges and subranges there-between, relative to the weight of the composition. These weights are on a dry weight basis.

The at least two latex polymers may be present in the composition in a weight ratio ranging from about 10:1 to about 1:10, or from about 1:5 to about 5:1, or from about 1:3 to about 3:1, or from about 0.5:1.5 to about 1:5, or from about 0.5:1.5 to about 1:3, including all ranges and subranges there-between.

In certain embodiments, the at least two latex polymers may be present in the composition in a weight ratio ranging from about 0.5:1.5 to about 3:1, or from about 0.5:1.5 to about 2:1, or from about 0.5:1.5 to about 1:1, including all ranges and subranges there-between.

In various embodiments, the at least two latex polymers may be identified as polymer A and polymer B. Compositions according to certain embodiments may comprise at least one polymer A and at least one polymer B, wherein both polymer A and polymer B are film-forming polymers. In additional embodiments, the at least two latex polymers may be chosen from polymers A, B, and C, wherein polymers A and B are film-forming polymers and polymer C is not a film-forming polymer. At least one of the latex polymers is chosen to be a film-forming polymer, for instance, various combinations of A and A; B and B; A and B; A and C; B and C; and A, B, and C, and the like may be used.

In various embodiments, polymer A may be chosen from latex polymers having a Young's modulus ranging from about 0.1 MPa to about 10 MPa and a strain, under stress at 0.5 MPa, of at least about 1%; and polymer B may be chosen from latex polymers having a Young's modulus ranging from about 10 MPa to about 6 GPa and a strain, under stress at 0.5 MPa, of less than about 5%. In at least certain embodiments, polymer A may have a glass transition temperature (Tg) ranging from about −90° C. to about 40° C., and polymer B may have a glass transition temperature (Tg) ranging from about 40° C. to about 200° C. In at least certain other embodiments, the weight ratio of polymer A to polymer B in the compositions of the invention is from about 1:5 to about 5:1, from about 1:3 to about 3:1, or from about 0.5:1.5 to about 1:3. In other embodiments, the weight ratio of polymer A to polymer B in the compositions of the invention is about 1:1. In yet other embodiments, the weight ratio of polymer A to polymer B in the compositions of the invention is about 0.5:1.5. Polymers A and B may be chosen from acrylate latex polymers and polyurethane latex polymers, with the proviso that when polymer A is chosen from an acrylate latex polymer, polymer B is chosen from a polyurethane latex polymer; and when polymer A is chosen from a polyurethane latex polymer, polymer B is chosen from an acrylate latex polymer.

In at least certain exemplary and non-limiting embodiments, latex polymers A and B may be chosen such that polymer A comprises at least one latex polymer that is a relatively soft, flexible latex polymer, and polymer B comprises at least one latex polymer that is a relatively hard, brittle polymer, although such characteristics are not required.

As used herein, a film-forming polymer is meant to include a polymer that is capable, by itself or in the presence of an auxiliary film-forming agent, of forming a macroscopically continuous film that adheres to keratin materials, and preferably a cohesive film, better still, a film whose cohesion and mechanical properties are such that said film can be isolated and manipulated individually, for example, when said film is prepared by pouring onto a non-stick surface such as Teflon-coated or silicone-coated surface. In addition, as used herein, a non-film-forming polymer is meant to include a polymer which will not form a film at ambient temperature or below, or in other words, will only form a film at temperatures above ambient. For purposes of this disclosure, ambient temperature is taken as being below 40° C. such as in the range of 15° C. to 30° C.

By "at least two latex polymers," it is contemplated that more than two latex polymers may be chosen. Thus, for example, in various embodiments, the composition may comprise polymers A and/or B, which are latex film-forming polymers, and the composition may also comprise at least one latex polymer C that is a non-film-forming polymer; and so on. However, as described, the at least two latex polymers are chosen from acrylate latex polymers and polyurethane latex polymers, with the proviso that when the first latex polymer is chosen from acrylate latex polymers, the second latex polymer is chosen from polyurethane latex polymers; and when the first latex polymer is chosen from polyurethane latex polymers, the second latex polymer is chosen from acrylate latex polymers.

In further embodiments, the composition comprises exactly two latex polymers, at least one of which is a film-forming polymer. According to additional embodiments, the composition comprises exactly two latex polymers, both of which are film-forming polymers. In yet further embodiments, the composition comprises at least two latex polymers, one or both of which are film-forming polymers, but does not comprise any additional film-forming polymers.

In at least certain embodiments of the invention, the at least two latex polymers are provided in the form of aqueous dispersions prior to formulating the compositions of the invention. In various embodiments, the aqueous dispersions may be obtained through an emulsion polymerization of monomers wherein the resulting latex polymers have a particle size lower than about 1 micron. In at least one exemplary embodiment, a dispersion prepared by the polymerization in water of one or more monomers having a polymerizable double bond may be chosen. In another exemplary embodiment, the aqueous dispersions obtained through an emulsion polymerization may be spray-dried.

In other embodiments, the latex polymers are produced from condensation reactions between monomers and subsequently dispersed in an aqueous medium.

Thus, the latex polymers may, in various exemplary embodiments, exist as dispersed polymer particles in a dispersion medium, such as an aqueous dispersion medium. The latex polymers may, in certain embodiments, each be dispersed in independent dispersion media. In yet further embodiments, the latex polymers may be dispersed together in the same dispersion medium.

The dispersion medium comprises at least one solvent chosen from water. The dispersion medium may further comprise at least one solvent chosen from cosmetically acceptable organic solvents. Cosmetically acceptable organic solvents may, in various embodiments, be water-miscible, e.g. capable of forming at 25° C. a homogeneous mixture that is transparent, or substantially transparent, to the eye. For instance, cosmetically acceptable organic solvents may be chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3-butylene glycol, dipropylene glycol, hexylene glycol, and glycerin; hydrocarbons, such as, for example, isododecane and mineral oil; and silicones, such as dimethicones, cyclomethicones, and cyclopentasiloxane; as well as mixtures thereof.

In at least one embodiment, the solvent of the dispersion medium consists of water. In other embodiments, the solvent of the dispersion medium consists of water and at least one cosmetically acceptable organic solvent. In further embodiments, the solvent comprises water. In yet further embodiments, the solvent of the dispersion medium primarily comprises water. For example, the solvent of the dispersion medium may, in at least certain exemplary embodiments, comprise greater than 50% water, such as greater than 55% water, greater than 60% water, greater than 65% water, greater than 70% water, greater than 75% water, greater than 80% water, greater than 85% water, greater than 90% water, greater than 95% water, greater than 96% water, greater than 97% water, greater than 98% water, or greater than 99% water.

In embodiments according to the invention, the latex polymer particles are not soluble in the solvent of the dispersion medium, i.e. are not water soluble and/or are not soluble in the at least one cosmetically acceptable organic solvent. Accordingly, the latex polymers retain their particulate form in the solvent or solvents chosen.

In at least certain exemplary embodiments, latex particles according to the invention may have an average diameter ranging up to about 1000 nm, such as from about 50 nm to about 800 nm, or from about 100 nm to about 500 nm. Such particle sizes may be measured with a laser granulometer (e.g. Brookhaven BI90).

In various embodiments, the latex polymers may, independently, be neutralized, partially neutralized, or unneutralized. In exemplary embodiments where the latex polymers are neutralized or partially neutralized, the particle size may be, for example, greater than about 800 nm. In at least certain embodiments, the particulate form of the latex polymers is retained in the dispersion medium.

In further embodiments, the latex polymers may be chosen from uncharged and charged latex polymers. Thus, the latex polymers may, according to various exemplary embodiments, be chosen from nonionic latex polymers, cationic latex polymers, and anionic latex polymers.

As non-limiting examples of latex polymers that may be used, mention may be made, independently, of acrylate latex polymers and polyurethane latex polymers.

In certain embodiments, when the first latex polymer is chosen from an acrylate latex polymer, the second latex polymer is chosen from a polyurethane latex polymer; and when the first latex polymer is chosen from a polyurethane latex polymer, the second latex polymer is chosen from an acrylate latex polymer.

In other embodiments, the first and second latex polymers may be chosen from acrylate latex polymers.

In yet other embodiments, the first and second latex polymers may be chosen from polyurethane latex polymers.

By way of non-limiting example only, one of the at least two latex polymers may be chosen from acrylate latex polymers, such as those resulting from the homopolymerization or copolymerization of monomers chosen from (meth)acrylics, (meth)acrylates, (meth)acrylamides and/or vinyl homopolymers or copolymers. The term "(meth)acryl" and variations thereof, as used herein, means acryl or methacryl.

The (meth)acrylic monomers may be chosen from, for example, acrylic acid, methacrylic acid, citraconic acid, itaconic acid, maleic acid, fumaric acid, crotonic acid, and maleic anhydride. Additional non-limiting examples of (meth)acrylic monomers include C1-C8 alkyl(meth)acrylic, such as, for example, methyl(meth)acrylic, ethyl(meth)acrylic, propyl(meth)acrylic, isopropyl(meth)acrylic, butyl(meth)acrylic, tert-butyl(meth)acrylic, pentyl(meth)acrylic, isopentyl(meth)acrylic, neopentyl(meth)acrylic, hexyl(meth)acrylic, isohexyl(meth)acrylic, 2-ethylhexyl(meth)acrylic, cyclohexyl(meth)acrylic, isohexyl(meth)acrylic, heptyl(meth)acrylic, isoheptyl(meth)acrylic, octyl(meth)acrylic, isooctyl(meth)acrylic, as well as combinations of any of the above.

The esters of (meth)acrylic monomers may be, by way of non-limiting example, C1-C8 alkyl(meth)acrylates such as methyl(meth)acrylate, ethyl(meth)acrylate, propyl(meth)acrylate, isopropyl(meth)acrylate, butyl(meth)acrylate, tert-butyl(meth)acrylate, pentyl(meth)acrylate, isopentyl(meth)acrylate, neopentyl(meth)acrylate, hexyl(meth)acrylate, isohexyl(meth)acrylate, 2-ethylhexyl(meth)acrylate, cyclohexyl(meth)acrylate, isohexyl(meth)acrylate, heptyl(meth)acrylate, isoheptyl(meth)acrylate, octyl(meth)acrylate, isooctyl(meth)acrylate, allyl(meth)acrylate, and combinations thereof. Additional and non-limiting examples include C1-C8 alkoxy(meth)acrylates, such as methoxy(meth)acrylate, ethoxy(meth)acrylate, propyl oxide(meth)acrylate, isopropyl oxide(meth)acrylate, butyl oxide(meth)acrylate, tert-butyl oxide(meth)acrylate, pentyl oxide(meth)acrylate, isopentyl oxide(meth)acrylate, neopentyl oxide(meth)acrylate. The esters may be, by way of non-limiting example, C2-C6 hydroxy alkyl(meth)acrylates, such as hydroxy ethyl(meth)acrylate, 2-hydroxypropyl(meth)acrylate, glycidyl(meth)acrylate, ethylene glycol di(meth)acrylate, polyethylene glycol mono(meth)acrylate, 1,4-butane diol di(meth)acrylate, 1,6,hexane diol di(meth)acrylate, and any combination thereof. The esters may be, by way of non-limiting example, aryl(meth)acrylates such as benzyl(meth)acrylate, phenyl(meth)acrylate, and any combination thereof. The esters can further contain amino groups such as aminoethyl(meth)acrylate, N,N-dimethylaminoethyl(meth)acrylate, N,N-dimethylaminopropyl(meth)acrylate, N,N-dimethylaminodimethylpropyl(meth)acrylate, N,N-diethyleaminoethyl(meth)acrylate, and N,N,N-trimethylaminoethyl(meth)acrylate; and salts of the ethylenic amines.

According to at least certain exemplary embodiments, the alkyl group of the esters may be either fluorinated or perfluorinated, e.g. some or all of the hydrogen atoms of the alkyl group are substituted with fluorine atoms. The monomers can also be fluorine-containing monomers, such as, by way of non-limiting example, trifluoroethyl methacrylate, 2,2,3,3-tetrafluoropropyl methacrylate, 2,2,3,3,4,4-hexafluorobutyl methacrylate, perfluorooctyl methacrylate and perfluorooctyl acrylate; and silicone macromonomers.

The amides of (meth)acrylic monomers can, for example, be made of (meth)acrylamides, and especially N-alkyl (meth)acrylamides, in particular N—(C1-C12) alkyl(meth) acrylates such as N-ethyl(meth)acrylamide, N-t-butyl(meth) acrylamide, N-t-octyl(meth)acrylamide, N-methylol(meth) acrylamide and N-diacetone(meth)acrylamide, and any combination thereof.

The vinyl monomers can include, but are not limited to, vinyl cyanide compounds such as acrylonitrile and methacrylonitrile; vinyl esters such as vinyl formate, vinyl acetate, vinyl propionate, vinyl neodecanoate, vinyl pivalate, vinyl benzoate and vinyl t-butyl benzoate, triallyl cyanurate; vinyl halides such as vinyl chloride and vinylidene chloride; aromatic mono- or divinyl compounds such as styrene, -methylstyrene, chlorostyrene, alkylstyrene, divinylbenzene and diallyl phthalate, and combination thereof. Other non-limiting ionic monomers can include para-styrensulfonic, vinylsulfonic, 2-(meth)acryloyloxyethylsulfonic, 2-(meth)acrylamido-2-methylpropylsulfonic acids.

The list of monomers given is not limiting, and it should be understood that it is possible to use any monomer known to those skilled in the art which includes acrylic and/or vinyl monomers (including monomers modified with a silicone chain).

Silicone acrylic polymers may also optionally be used as vinyl polymer in at least one exemplary and non-limiting embodiment.

In at least certain, non-limiting exemplary embodiments, acrylic latex polymers may be chosen from aqueous dispersions of Methacrylic Acid/Ethyl Acrylate copolymer (INCI: Acrylates Copolymer, such as LUVIFLEX® Soft by BASF), PEG/PPG-23/6 Dimethicone Citraconate/C10-30 Alkyl PEG-25 Methacrylate/Acrylic Acid/Methacrylic Acid/Ethyl Acrylate/Tri methylolpropane PEG-15 Triacrylate copolymer (INCI: Polyacrylate-2 Crosspolymer, such as FIXATE SUPERHOLD™ by Lubrizol), Styrene/Acrylic copolymer (such as NEOCRYL® A-1120, DSM), Ethylhexyl Acrylate/Methyl Methacrylate/Butyl Acrylate/Acrylic Acid/Methacrylic Acid copolymer (INCI: Acrylates/Ethylhexyl Acrylate Copolymer, such as Daitosol 5000SJ, Daito Kasei Kogyo), Acrylic/Acrylates Copolymer (INCI name: Acrylates Copolymer, such as DAITOSOL 5000AD, Daito Kasei Kogyo), Vinyl Acetate Acrylic Ester Copolymer (INCI name: Acrylates/VA Copolymer, such as VINYSOL 2140, Daido Chemical) and Acrylates Copolymers, such as those known under the tradename ACULYN™ 33 (Dow Chemical), under the tradename LUVIMER® MAE (BASF), or under the tradename BALANCE CR (AKZO NOBEL), Styrene/Acrylates Copolymer, known under the tradename JONCRYL 77 from BASF, Styrene/Acrylates/Ammonium Methacrylate Copolymer, known under the tradename SYN-TRAN PC5620 CG from Interpolymer, and mixtures thereof.

In yet further exemplary and non-limiting embodiments, one of the at least two latex polymers may be chosen from polyurethane latex polymers, such as aqueous polyurethane dispersions comprising the reaction products of (i), (ii), and/or (iii), defined below.

Reaction product (i) may be any prepolymer according to the formula:

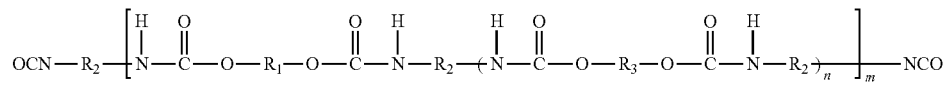

wherein R1 is chosen from bivalent radicals of a dihydroxyl functional compound, R2 is chosen from hydrocarbon radicals of an aliphatic or cycloaliphatic polyisocyanate, and R3 is chosen from radicals of a low molecular weight diol, optionally substituted with ionic groups, n ranges from about 0 to about 5, and m is greater than about 1.

Suitable dihydroxyl compounds for providing the bivalent radical R1 include those having at least two hydroxy groups, and having number average molecular weights ranging from about 700 to about 16,000, such as, for example, from about 750 to about 5000. Non-limiting examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. In various embodiments, polyester polyols, polyether polyols, and polyhydroxy polycarbonates may be chosen. Mixtures of such compounds are also within the scope of the invention.

The polyester diol(s) may optionally be prepared from aliphatic, cycloaliphatic, or aromatic dicarboxylic or polycarboxylic acids, or anhydrides thereof; and dihydric alcohols such as diols chosen from aliphatic, alicyclic, or aromatic diols.

The aliphatic dicarboxylic or polycarboxylic acids may be chosen from, for example: succinic, fumaric, glutaric, 2,2-dimethylglutaric, adipic, itaconic, pimelic, suberic, azelaic, sebacic, maleic, malonic, 2,2-dimethylmalonic, nonanedicarboxylic, decanedicarboxylic, dodecane⌐ dioic, 1,3-cyclohexanedicarboxylic, 1,4-cyclo⌐ hexane-dicarboxylic, 2,5-norboranedicarboxylic, diglycolic, thiodipropionic, 2,5-naphthalene-dicarboxylic, 2,6-naphthalene⌐ dicarboxylic, phthalic, terephthalic, isophthalic, oxanic, o-phthalic, tetrahydrophthalic, hexahydrophthalic or trimellitic acid.

The acid anhydrides may, in further exemplary embodiments, be chosen from o-phthalic, trimellitic or succinic acid anhydride or a mixture thereof. By way of non-limiting example only, the dicarboxylic acid may be adipic acid.

The dihydric alcohols may be chosen from, for example, ethanediol, ethylene glycol, diethylene glycol, triethylene glycol, trimethylene glycol, tetraethylene glycol, 1,2-propanediol, dipropylene glycol, tripropylene glycol, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, cyclohexanedimethanol, 1,8-octanediol, 1,10-decanediol, 1,12-dodecanediol, neopentyl glycol, and mixtures thereof. The cycloaliphatic and/or aromatic dihydroxyl compounds may also be suitable as the dihydric alcohol(s) for the preparation of the polyester polyol(s).

The polyester diols may also be chosen from homopolymers or copolymers of lactones, which are, in at least certain embodiments, obtained by addition reactions of lactones or lactone mixtures, such as butyrolactone, ε-caprolactone and/or methyl-ε-caprolactone with the appropriate polyfunctional, e.g. difunctional, starter molecules such as, for example, the dihydric alcohols mentioned above. The corresponding polymers of ε-caprolactone may be chosen in at least some embodiments.

The polyester polyol, e.g. polyester diol, radical R1, may be obtained by polycondensation of dicarboxylic acids, such as adipic acid, with polyols, e.g. diols, such as hexanediol, neopentyl glycol, and mixtures thereof.

The polycarbonates containing hydroxyl groups comprise those known per se, such as the products obtained by reacting diols, such as (1,3)-propanediol, (1,4)-butanediol and/or (1,6)-hexanediol, diethylene glycol, triethylene glycol, or tetraethylene glycol with diaryl carbonates, for example diphenyl carbonate or phosgene.

Optional polyether polyols may be obtained in any known manner by reacting starting compounds which contain reactive hydrogen atoms with alkylene oxides, such as, for example, ethylene oxide; propylene oxide; butylene oxide; styrene oxide; tetrahydrofuran; or epichlorohydrin, or with mixtures of these alkylene oxides. In at least certain embodiments, the polyethers do not contain more than about 10% by weight of ethylene oxide units. For example, polyethers obtained without addition of ethylene oxide may be chosen.

Polyethers modified with vinyl polymers are also suitable according to various embodiments of the invention. Products of this type can be obtained by polymerization, for example, of styrene and acrylonitrile in the presence of polyethers, for example as described in U.S. Pat. Nos. 3,383,351; 3,304,273; 3,523,095; 3,110,695; and German patent 1 152 536.

Among the polythioethers which may be chosen include the condensation products obtained from thiodiglycol per se and/or with other glycols, dicarboxylic acids, formaldehyde, aminocarboxylic acids, and/or amino alcohols. The products obtained are either mixed polythioethers, polythioether esters, or polythio¬ether ester amides, depending on the co-components.

Optional polyacetals include but are not limited to the compounds which can be prepared from aldehydes, for example formaldehyde, and from glycols, such as diethylene glycol, triethylene glycol, ethoxylated 4,4'-(dihydroxy)diphenyl-dimethylmethane, and (1,6)-hexane¬diol. Polyacetals useful according to various non-limiting embodiments of the invention can also be prepared by polymerization of cyclic acetals.

Optional polyhydroxy polyesteramides and polyamines include, for example, the mainly linear condensation products obtained from saturated or unsaturated, polybasic carboxylic acids or anhydrides thereof, and from saturated or unsaturated, polyvalent amino alcohols, from diamines, or from polyamines, as well as mixtures thereof.

Optional monomers for the production of polyacrylates having hydroxyl functionality comprise acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate, and 2-isocyanatoethyl methacrylate.

Mixtures of dihydroxy compounds can also be chosen.

Optional polyisocyanates for providing the hydrocarbon-based radical R2 include, for example, organic diisocyanates having a molecular weight ranging from about 100 to about 1500, such as about 112 to about 1000, or about 140 to about 400.

Optional diisocyanates are those chosen from the general formula R2(NCO)2, in which R2 represents a divalent aliphatic hydrocarbon group comprising from about 4 to 18 carbon atoms, a divalent cycloaliphatic hydrocarbon group comprising from about 5 to 15 carbon atoms, a divalent araliphatic hydrocarbon group comprising from about 7 to 15 carbon atoms, or a divalent aromatic hydrocarbon group comprising from about 6 to 15 carbon atoms. Examples of the organic diisocyanates which may be chosen include, but are not limited to, tetramethylene diisocyanate, 1,6-hexamethylene diisocyanate, dodecamethylene diisocyanate, cyclohexane-1,3-diisocyanate and cyclohexane-1,4-diisocyanate, 1-isocyanato-3-isocyanato¬methyl-3,5,5-trimethylcyclohexane (isophorone diisocyanate or IPDI), bis(4-isocyanatocyclohexyl)-methane, 1,3-bis(isocyanatomethyl)cyclohexane and 1,4-bis(isocyanatomethyl)cyclohexane and bis(4-isocyanato-3-methylcyclohexyl)methane. Mixtures of diisocyanates can also be used.

In at least certain embodiments, diisocyanates are chosen from aliphatic and cycloaliphatic diisocyanates. For example, 1,6-hexamethylene diisocyanate, isophorone diisocyanate, and dicyclohexylmethane diisocyanate, as well as mixtures thereof may be chosen.

The use of diols, for example low molecular weight diols, R3, may in at least certain embodiments allow a stiffening of the polymer chain. The expression "low molecular weight diols" means diols having a molecular weight ranging from about 50 to about 800, such as about 60 to 700, or about 62 to 200. They may, in various embodiments, contain aliphatic, alicyclic, or aromatic groups. In certain exemplary embodiments, the compounds contain only aliphatic groups. The diols that may be chosen may optionally have up to about 20 carbon atoms, and may be chosen, for example, from ethylene glycol, diethylene glycol, propane-1,2-diol, propane-1,3-diol, butane-1,4-diol, 1,3-butylene glycol, neopentyl glycol, butylethylpropanediol, cyclohexanediol, 1,4-cyclohexanedimethanol, hexane-1,6-diol, bisphenol A (2,2-bis(4-hydroxyphenyl)propane), hydrogenated bisphenol A (2,2-bis(4-hydroxy¬cyclo¬hexyl)-propane), and mixtures thereof. For example, R3 may be derived from neopentyl glycol.

Optionally, the low molecular weight diols may contain ionic or potentially ionic groups. Suitable low molecular weight diols containing ionic or potentially ionic groups may be chosen from those disclosed in U.S. Pat. No. 3,412,054. In various embodiments, compounds may be chosen from dimethylohbutanoic acid (DMBA), dimethylolpropionic acid (DMPA), and carboxyl-containing caprolactone polyester diol. If low molecular weight diols containing ionic or potentially ionic groups are chosen, they may, for example, be used in an amount such that less than about 0.30 meq of —COOH is present per gram of polyurethane in the polyurethane dispersion. In at least certain exemplary and non-limiting embodiments, the low molecular weight diols containing ionic or potentially ionic groups are not used.

Reaction product (ii) may be chosen from at least one chain extender according to the formula:

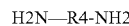

wherein R4 is chosen from alkylene or alkylene oxide radicals, said radicals not being substituted with ionic or potentially ionic groups.

Reaction product (ii) may optionally be chosen from alkylene diamines, such as hydrazine, ethylene diamine, propylenediamine, 1,4-butylenediamine and piperazine; and alkylene oxide diamines such as dipropylamine diethylene glycol (DPA-DEG available from Tomah Products, Milton, Wis.), 2-methyl-1,5-pentanediamine (Dytec A from DuPont), hexanediamine, isophorone diamine, and 4,4-methylenedi(cyclohexylamine), and the DPA-series of ether amines available from Tomah Products, Milton, Wis., including dipropylamine propylene glycol, dipropylamine dipropylene glycol, dipropylamine tripropylene glycol, dipropylamine poly(propylene glycol), dipropylamine ethylene glycol, dipropylamine poly(ethylene glycol), dipropylamine 1,3-propanediol, dipropylamine 2-methyl-1,3-propanediol, dipropylamine 1,4-butanediol, dipropylamine 1,3-butanediol, dipropylamine 1,6-hexanediol and dipropylamine cyclohexane-1,4-dimethanol, and mixtures thereof.

Reaction product (iii) may be chosen from at least one chain extender according to the formula:

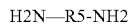

H2N—R5-NH2 wherein R5 is chosen from alkylene radicals substituted with ionic or potentially ionic groups. In at least certain exemplary embodiments, the compounds may have an ionic or potentially ionic group and two isocyanate-reactive groups.

As used herein, ionic or potentially ionic groups may include groups comprising ternary or quaternary ammonium groups, groups convertible into such groups, carboxyl groups, carboxylate groups, sulphonic acid groups, and sulphonate groups. At least partial conversion of the groups convertible into salt groups of the type mentioned may take place before or during the mixing with water. Specific compounds include diaminosulphonates, such as for example the sodium salt of N-(2-aminoethyl)-2-aminoethanesulphonic acid (AAS) or the sodium salt of N-(2-aminoethyl)-2-aminopropionic acid.

In at least certain embodiments, R5 represents an alkylene radical substituted with sulphonic acid or sulphonate groups. By way of example only, the compound is chosen from sodium salts of N-(2-aminoethyl)-2-aminoethanesulphonic acid.

By way of non-limiting example, such latexes include, but are not limited to, aqueous polyurethane dispersions comprising a reaction product of a prepolymer such as, for example, those sold under the BAYCUSAN® name by Bayer such as, for example, BAYCUSAN® C1000 (INCI name: Polyurethane-34), BAYCUSAN® C1001 (INCI name: Polyurethane-34), BAYCUSAN® C1003 (INCI name: Polyurethane-32), BAYCUSAN® C1004 (INCI name: Polyurethane-35) and BAYCUSAN® C1008 (INCI name: Polyurethane-48). In various exemplary embodiments, polyurethane latexes may be chosen from, but are not limited to, aqueous polyurethane dispersion of Isophthalic Acid/Adipic Acid/Hexylene Glycol/Neopentyl glycol/Dimethylolpropanoic Acid/Isophorone Diisocyanate copolymer (INCI name: Polyurethane-1, such as LUVISET® P.U.R, BASF), polycarbonate polyurethane, aliphatic polyurethane and aliphatic polyester polyurethane (such as the NEOREZ® series, DSM, such as NEOREZ® R989 (INCI name: Polvcarbamyl Polyglycol Ester), and NEOREZ® R-2202).

In at least certain embodiments, the at least two latex polymers may be chosen from polyacrylic latex, polyacrylate latex, polystyrene latex, polyester latex, polyamide latex, polyurea latex, polyurethane latex, epoxy resin latex, and their copolymers.

In various embodiments according to the invention, it may be possible to choose a polymer that comprises both acrylate and polyurethane parts at the molecular level.

In some embodiments, the at least two latex polymers of the present invention comprise polyurethane latex polymers and acrylate latex copolymers.

In other embodiments, the at least two latex polymers of the present invention comprise polyurethane latex polymers chosen from aliphatic polyurethane, polycarbonate polyurethane, aliphatic polyester polyurethane polyurethane-32, polyurethane-34, polyurethane-35, polyurethane-48, and mixtures thereof and acrylate latex copolymers chosen from Acrylates copolymer, Polyacrylate-2 Crosspolymer, Acrylates/Hydroxyesters Acrylate Copolymer, Acrylate/Ethylhexyl Acrylate Copolymer, Styrene Acrylate Copolymer, Acrylate/VA Copolymer, Styrene/Acrylic copolymer, Styrene/Acrylates/Ammonium Methacrylate Copolymer and mixtures thereof.

In certain embodiments, the at least two latex polymers of the present invention comprise polyurethane-34 and acrylates copolymer.

In some embodiments, the at least two latex polymers of the present invention comprise polymer A and polymer B wherein polymer A is preferably chosen from polyurethane latex polymers and polymer B is preferably chosen from acrylate latex polymers.

Silicone Organic Polymer Compound

The at least one silicone-organic polymer compound of the present invention includes, but is not limited to, a silicone polyvinyl acetate compound.

The silicone-organic polymer hybrid compound of the present invention may also be chosen from a cross-linked anionic copolymer comprised of organic polymer blocks and silicone blocks, resulting in a multiblock polymer structure.

In particular, the silicone-organic polymer compound of the present invention may be chosen from cross-linked anionic copolymers comprising at least one cross-linked polysiloxane structural unit. Examples of these polymers have been described in the PCT publication, WO2011069786, published Jun. 16, 2011.

A particularly preferred silicone-organic polymer compound of the present invention is a compound having the INCI name of Crotonic Acid/Vinyl C8-12 Isoalkyl Esters/VA/Bis-Vinyldimethicone Crosspolymer which is a copolymer of Crotonic Acid, vinyl C8-12 isoalkyl esters and Vinyl Acetate crosslinked with bis-vinyldimethicone. This compound is commercially available from the company Wacker Chemie AG under the tradename Wacker Belsil® P1101 (may also be known under the tradename Wacker Belsil® P101). Crotonic Acid/Vinyl C8-12 Isoalkyl Esters/VA/Bis-Vinyldimethicone Crosspolymer is also known by the technical name of Crotonic Acid/Vinyl C8-12 Isoalkyl Esters/VA/divinyldimethicone Crosspolymer.

The at least one silicone-organic polymer compound is present in the composition of the present invention in an amount, on a dry weight basis, of from about 0.5 to about 10% by weight, preferably from about 0.5 to about 6% by weight, more preferably from about 1 to about 5% by weight, or even more preferably from about 2 to about 4% by weight, including all ranges and subranges there-between, relative to the weight of the composition. These weights are on a dry weight basis.

The silicone-organic polymer compound is neutralized in order to remain solubilized in the composition of the present invention. Representative examples of neutralizers useful for this purpose include AMP (aminomethyl propanol), AMPD (aminomethyl propanediol), TIPA (triisopropanol amine), Sodium/Potassium hydroxides, Dimethylsterarylamine, Dimethyl/tallowamine lysine, ornithine, arginine, glutamic and aspartic acid. The amount of neutralizer is selected on criteria that include the desired pH of the composition. Thus, the amount of neutralizer generally ranges from greater than 0 (e.g., about 0.01%) to about 3%, and in some embodiments from 0.05% to about 2%, by weight, including all ranges and subranges there-between, relative to the weight of the composition.

In certain embodiments of the present invention, the silicone-organic polymer compound is partially neutralized, that is from 80% to less than 100% neutralized. For example, the silicone-organic polymer compound can be 80%, or 85%, or 90%, or 95% neutralized. Thus, in certain embodiments, the amount of the neutralizing agent is such that a desired of degree of neutralization can be achieved.

In other embodiments of the present invention, the silicone-organic polymer compound is at least 80% neutralized.

Ratio of Polyurethane Latex Polymer to Silicone-Organic Polymer Compound

In some embodiments of the present invention, the weight ratio, on a dry weight basis, of the polyurethane latex polymer to the silicone-organic polymer compound is less than about 2, or ranges from about 0.1 to about 1.75 or preferably from about 0.15 to about 1.5 or more preferably from about 0.25 to about 1.1, including all ranges and subranges there-between.

In other embodiments, the weight ratio, on a dry weight basis, of the polyurethane latex polymer to the silicone-organic polymer compound ranges from about 0.235 to about 1.06, or is at about 0.25, or about 0.4, or about 0.5, or about 0.8, or about 1.

In preferred embodiments, the weight ratio, on a dry weight basis, of the polyurethane latex polymer to the silicone-organic polymer compound is at about 2:4 (or 0.5) or at about 2:2 (or 1) or at about 1:2.5 (or 0.4).

Ratio of Latex Polymers to Silicone Organic Polymer Compound

In certain embodiments, the weight ratio of the total amount of the latex polymers to the amount of the silicone-organic polymer in the compositions of the invention ranges from about 1 to about 0.25, including all ranges and subranges there-between.

In other embodiments, the weight ratio of the total amount of the latex polymers to the amount of the silicone-organic polymer in the compositions of the invention ranges from about 2:1 to about 2:4, or preferably from about 2:1 to about 2:3, or more preferably from about 2:2 to about 2:4, including all ranges and subranges there-between.

In yet other embodiments, the weight ratio of the total amount of the latex polymers to the amount of the silicone-organic polymer in the compositions of the invention is at about 1:2, or at about 1:4, or at about 2:1, or at about 2:2, or at about 2:4.

Cosmetically Acceptable Carrier

The cosmetically acceptable carrier of the present invention comprises a solvent chosen from water, at least one organic solvent or combinations thereof.

The cosmetically acceptable carrier of the present invention may be comprised of water alone.

The cosmetically acceptable carrier of the present invention may also comprise mixtures of water and at least one organic solvent.

Suitable organic solvents may be chosen from volatile and nonvolatile organic solvents.

Suitable organic solvents are typically C1-C4 lower alcohols, glycols, polyols, polyol ethers, hydrocarbons, and oils.

Examples of organic solvents include, but are not limited to, ethanol, isopropyl alcohol, benzyl alcohol, phenyl ethyl alcohol, propylene glycol, pentylene glycol, hexylene glycol, glycerol, and mixtures thereof.

Other suitable organic solvents include glycol ethers, for example, ethylene glycol and its ethers such as ethylene glycol monomethyl ether, ethylene glycol monopropyl ether, ethylene glycol monobutyl ether, propylene glycol and its ethers, such as propylene glycol monomethyl ether, propylene glycol monopropyl ether, propylene glycol monobutyl ether, dipropylene glycol and diethylene glycol alkyl ethers, such as diethylene glycol monoethyl ether, diethylene glycolmonobutyl ether, and dipropylene glycol n-butyl ether. Glycol ethers are commercially available from The Dow Chemical Company under the DOW E-series and DOW P-series. One preferred glycol ether for use in the present invention is dipropylene glycol n-butyl ether, known under the tradename of DOWANOL DPnB.

Suitable organic solvents also include synthetic oils and hydrocarbon oils include mineral oil, petrolatum, and $C_{10}$-$C_{40}$ hydrocarbons which may be aliphatic (with a straight, branched or cyclic chain), aromatic, arylaliphatic such as paraffins, iso-paraffins, isododecanes, aromatic hydrocarbons, polybutene, hydrogenated polyisobutene, hydrogenated polydecene, polydecene, squalene, petrolatum and isoparaffins, silicone oils, fluoro oils and mixtures, thereof.

The term "hydrocarbon-based oil" or "hydrocarbon oil" refers to oil mainly containing hydrogen and carbon atoms and possibly oxygen, nitrogen, sulfur and/or phosphorus atoms. Representative examples of hydrocarbon-based oils include oils containing from 8 to 16 carbon atoms, and especially branched C8-C16 alkanes (also known as isoparaffins), for instance isododecane (also known as 2,2,4,4,6-pentamethylheptane), isodecane and isohexadecane.

Examples of silicone oils that may be useful in the present invention include nonvolatile silicone oils such as polydimethylsiloxanes (PDMS), polydimethylsiloxanes comprising alkyl or alkoxy groups that are pendent and/or at the end of a silicone chain, these groups each containing from 2 to 24 carbon atoms, phenyl silicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates, and dimethicones or phenyltrimethicones with a viscosity of less than or equal to 100 cSt.

Other representative examples of silicone oils that may be useful in the present invention include volatile silicone oils such as linear or cyclic silicone oils, especially those with a viscosity ÿ centistokes (8×10-6 m 2/s) and especially containing from 2 to 10 silicon atoms and in particular from 2 to 7 silicon atoms, these silicones optionally comprising alkyl or alkoxy groups containing from 1 to 10 carbon atoms. Specific examples include dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Representative examples of fluoro oils that may be suitable for use in the present invention include volatile fluoro oils such as nonafluoromethoxybutane and perfluoro-methylcyclopentane.

The amount of the organic solvent/compound present in the compositions of the present invention can range from about 0.5% to about 95%, or from about 0.5% to about 80%, or from about 0.5% to about 60%, or from about 0.5% to about 40%, or from about 0.5% to about 30%, or from about 0.5% to about 20%, and in some embodiments, from about 0.5% to about 15%, by weight, or preferably from about 1% to about 10%, by weight, or more preferably from about 1.5% to about 8%, by weight, or even more preferably, from about 2% to about 6%, by weight, including all ranges and subranges there-between, relative to the total weight of the composition.

In some embodiments, the amount of the organic solvent/compound present in the compositions of the present invention can range from about 1% to about 6%, by weight, or preferably from about 1.5% to about 5.5%, by weight, or more preferably from about 1.5% to about 5%, by weight, or even more preferably, from about 2% to about 4%, by weight, including all ranges and subranges there-between, relative to the total weight of the composition In other embodiments, the amount of the organic solvent/compound present in the compositions of the present invention is at about 2%, about 2.5%, about 3%, about 3.5%, about 4%, about 4.5%, about 5%, about 5.5% or about 6% by weight, relative to the total weight of the composition.

In certain embodiments, compositions of the present invention comprise both water and organic solvents/compounds selected from volatile organic solvents, non-volatile organic solvents, and mixtures thereof.

Preferred examples of organic solvents/compounds include volatile organic solvents such as C2 to C4 monoalcohols, such as ethanol, isopropyl alcohol, butanol, polyols such as C2-C6 glycols e.g., propylene glycol, butylene glycol, pentylene glycol, hexylene glycol, glycerol, isododecane, volatile polyol ethers, volatile glycol ethers, acetone, propylene carbonate, benzyl alcohol, and mixtures thereof. In certain embodiments, it is preferred that the amount of volatile organic solvent/compound does not exceed 55% by weight, relative to the weight of the composition of the present invention.

In other certain embodiments, it is preferred that the amount of volatile organic solvent/compound does not exceed 20% by weight, relative to the weight of the composition of the present invention.

In yet other certain embodiments, it is preferred that the amount of volatile organic solvent/compound does not exceed 10% by weight, relative to the weight of the composition of the present invention.

In preferred embodiments, the amount of volatile organic solvent/compound does not exceed 6% by weight, relative to the weight of the composition of the present invention.

In other preferred embodiments, the amount of volatile organic solvent/compound does not exceed 5% by weight, relative to the weight of the composition of the present invention.

In yet other preferred embodiments, the amount of volatile organic solvent/compound does not exceed 4% by weight, relative to the weight of the composition of the present invention.

Other preferred examples of organic solvents/compounds include nonvolatile organic solvents such as hydrocarbons such as straight chain hydrocarbons, nonvolatile silicone oils, mineral oil, polybutene, hydrogenated polyisobutene, hydrogenated polydecene, polydecene, squalene, petrolatum, isoparaffins, nonvolatile glycol ethers, and mixtures, thereof.

In certain embodiments, it is preferred that the amount of nonvolatile organic solvent/compound does not exceed 40% by weight, relative to the weight of the composition of the present invention.

In other certain embodiments, it is preferred that the amount of nonvolatile organic solvent/compound does not exceed 20% by weight, relative to the weight of the composition of the present invention.

In yet other certain embodiments, it is preferred that the amount of nonvolatile organic solvent/compound does not exceed 10% by weight, relative to the weight of the composition of the present invention.

In preferred embodiments of the present invention, the at least one organic solvent is chosen from ethanol, glycol ether, for example, dipropylene glycol n-butyl ether, known under the tradename of DOWANOL DPnB, isododecane, mineral oil, propylene glycol, pentylene glycol, hexylene glycol, glycerol, and mixtures thereof.

In certain embodiments of the present invention, the at least one organic solvent is chosen from ethanol.

The organic solvents may also comprise the solvent of the dispersion medium employed to disperse the latex polymers and silicone organic polymer compound of the present invention.

In some embodiments, the cosmetically acceptable carrier in the compositions of the present invention contains water in the amount of about 95%, 90%, 80%, 70%, 60%, 50%, 40%, 30%, 20%, 10%, 5% by weight or less, based on the total weight of the compositions. Additionally, the cosmetically acceptable carrier in the compositions of the present invention can contain water in the amount of from about 20% to about 95% by weight, or from about 50% to about 90% by weight, or from about 60% to about 80% by weight, relative to the weight of the compositions.

In other embodiments, the cosmetically acceptable carrier in the compositions of the present invention contains water in the amount of at least about 95%, 90%, 80%, 70%, 60%, 50%, 40%, 30%, 20%, 10%, 5% by weight or less, based on the total weight of the compositions.

In yet some other embodiments, the cosmetically acceptable carrier of the present invention does not comprise water that is added as a separate ingredient, by itself, into the compositions of the present invention, such that water is present in the compositions of the present invention when it accompanies one or more ingredients of a raw material that is added into the compositions of the invention.

The compositions described above are useful for application onto keratinous substrates such as hair on the head of human individuals.

Thus, the compositions of the present invention can be made into various cosmetic products such hair care products, hair styling products, and make up products.

Representative types of hair care compositions, including hair cosmetic and styling compositions, of the present invention include compositions for shaping the hair, maintaining the shape of the hair, styling products (e.g., gels, creams, milks, pastes, waxes, ointments, serums, foams, hair lotions, mousses, pump-sprays, non-aerosol sprays and aerosol sprays), pre-treatments and post-treatments for color protection, conditioning or protection from heat damage, leave-in hair treatments, rinse-off hair treatments, combination shampoo/styling compositions and hair volumizing compositions.

The compositions of the present invention can be in the form of an aqueous composition or an emulsion, such as a lotion or cream.

In some embodiments, the composition of the present invention can be the form of a wax, spray wax, or a paste.

Auxiliary Ingredients

The compositions of the present invention may further comprise auxiliary ingredients selected from propellants, rheology modifiers, surfactants, lipohilic compounds, skin and hair active agents, sunscreens, preservatives, fragrances, pH adjusting agents, and mixtures thereof.

In one embodiment, the composition of the present invention is in the form of an aerosol spray, comprising a propellant.

Representative examples of propellants include C3 to C5 alkanes such as n-butane, isobutane, and propane, dimethyl ether (available commercially from Harp Intl under the tradename HARP DME), C2-C5 halogenated hydrocarbons, e.g., 1,1-difluoroethane (available commercially from DuPont under the tradename DYMEL 152a), difluoroethane, chlorodifluoroethane, chlorodifluoromethane, air, nitrogen, carbon dioxide, and mixtures thereof. The amount of the propellant can range from about 3 to about 90%, and in some embodiments from about 3 to about 60%, by weight, or such as from about 3 to about 20% by weight, or such as from about 3 to about 10% by weight, or such as from about 3 to about 6% by weight, including all ranges and subranges there-between, relative to the weight of the composition.

Accordingly, the compositions of the present invention may contain at least one auxiliary ingredient, which as those skilled in the cosmetics art will appreciate, is chosen based on several criteria, including for example, the type of product and its intended use and effect, compatibility with the other ingredients, and aesthetic appeal. Representative types of such additional ingredients include rheology modifiers (also known as gelling agents or thickeners), nonionic surfactants, lipophilic compounds such as oils and waxes, and hair and skin active ingredients. Examples of these ingredients are described herein.

Rheology Modifiers

Broadly, the rheology modifier(s) that may be useful in the practice of the present invention include those conventionally used in cosmetics such as polymers of natural origin and synthetic polymers.

Representative rheology-modifying agents that may be used in the practice of the present invention include non-ionic, anionic, cationic, and amphoteric polymers, and other rheology modifiers such as cellulose-based thickeners (e.g., hydroxyethylcellulose, hydroxypropylcellulose, carboxymethylcellulose, cationic cellulose ether derivatives, quaternized cellulose derivatives, etc.), guar gum and its derivatives (e.g., hydroxypropyl guar, cationic guar derivatives, etc.), gums such as gums of microbial origin (e.g., xanthan gum, scleroglucan gum, etc.), and gums derived from plant exudates (e.g., gum arabic, ghatti gum, karaya gum, gum tragacanth, carrageenan gum, agar gum and carob gum), pectins, alginates, and starches, crosslinked homopolymers of acrylic acid or of acrylamidopropane-sulfonic acid, associative polymers, non-associative thickening polymers, and water-soluble thickening polymers.

In some embodiments, the rheology-modifying agent includes a polymer chosen from nonionic, anionic, cationic and amphoteric amphiphilic polymers.

The rheology-modifying agents may also be chosen from associative celluloses include quaternized cationic celluloses and quaternized cationic hydroxyethylcelluloses modified by groups containing at least one hydrophobic chain, such as alkyl, arylalkyl or alkylaryl groups containing at least 8 carbon atoms, and mixtures thereof.

The alkyl radicals carried by the above quaternized celluloses or hydroxyethylcelluloses may, in various embodiments, comprise from 8 to 30 carbon atoms. The aryl radicals may, for example, denote the phenyl, benzyl, naphthyl or anthryl groups. Representative examples of quaternized alkylhydroxy-ethylcelluloses containing a C8-C30 hydrophobic chain include the products Quatrisoft LM 200®, Quatrisoft LM-X 529-18-A®, Quatrisoft LM-X 529-18B® (C12 alkyl) and Quatrisoft LM-X 529-8® (Ci8 alkyl) sold by Amerchol and the products Crodacel QM®, Crodacel QL® (C12 alkyl) and Crodacel QS® (Ci8 alkyl) sold by Croda.

Representative examples of nonionic cellulose derivatives include hydroxyethylcelluloses modified by groups comprising at least one hydrophobic chain, such as alkyl, arylalkyl or alkylaryl groups, or their blends, and in which the alkyl groups are, for example, C8-C22 alkyl groups, such as the product Natrosol Plus Grade 330 CS® (C16 alkyls) sold by Aqualon or the product Bermocoll EHM 100® sold by Berol Nobel.

Representative examples of cellulose derivatives modified by alkylphenyl polyalkylene glycol ether groups include the product Amercell Polymer HM-1500® sold by Amerchol.

The rheology-modifying agent is typically present in an amount ranging from about 0.01% to about 10% by weight, in some embodiments from about 0.1% to about 5% by weight, including all ranges and subranges there-between, relative to the weight of the composition.

The compositions of the present invention may further comprise compounds such as gellifying and viscosity modifying agents which may aid in improving the viscosity of the compositions.

Surfactants

The compositions of the present invention can further comprise at least one surfactant selected from nonionic surfactants.

Non-limiting examples of nonionic surfactants includes alkoxylated derivatives of the following: fatty alcohols, alkyl phenols, fatty acids, fatty acid esters and fatty acid amides, wherein the alkyl chain is in the C12-50 range, typically in the C16-40 range, more typically in the C24 to C40 range, and having from about 1 to about 110 alkoxy groups. The alkoxy groups are selected from the group consisting of C2-C6 oxides and their mixtures, with ethylene oxide, propylene oxide, and their mixtures being the typical alkoxides. The alkyl chain may be linear, branched, saturated, or unsaturated. Of these alkoxylated non-ionic surfactants, the alkoxylated alcohols are typical, and the ethoxylated alcohols and propoxylated alcohols are more typical. The alkoxylated alcohols may be used alone or in mixtures with those alkoxylated materials disclosed hereinabove.

Examples of fatty alcohols are lauryl alcohol, cetyl alcohol, stearyl alcohol, cetearyl alcohol, and behenyl alcohol.

Commercially available nonionic surfactants are Brij® nonionic surfactants from Croda, Inc., Edison, N.J. Typically, Brij® is the condensation products of aliphatic or fatty alcohols with from about 1 to about 54 moles of ethylene oxide, the alkyl chain of the alcohol being typically a linear chain and having from about 8 to about 22 carbon atoms, for example, Brij® 72 (i.e., Steareth-2) and Brij® 76 (i.e., Steareth-10).

Also useful herein as nonionic surfactants are alkyl glycosides or alkylpolyglycosides (alkylpolyglucosides) which are the condensation products of long chain alcohols, which are the condensation products of long chain alcohols, e.g. C8-C30 alcohols, with sugar or starch polymers. These compounds can be represented by the formula $(S)_n$-O-R wherein S is a sugar moiety such as glucose, fructose, mannose, galactose, and the like; n is an integer of from about 1 to about 1000, and R is a C8-C30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a C8-C20 alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein sucrose ester surfactants such as sucrose cocoate and sucrose laurate.

Other nonionic surfactants suitable for use in the present invention are glyceryl esters and polyglyceryl esters, including but not limited to, glyceryl monoesters, typically glyceryl monoesters of C16-C22 saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of C16-C22 saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of C16-C22 saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from Croda, Inc., Edison, N.J.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Also suitable for use as nonionic surfactants are alkoxylated derivatives of glyceryl esters, sorbitan esters, and alkyl polyglycosides, wherein the alkoxy groups are selected from the group consisting of C2-C6 oxides and their mixtures, with ethoxylated or propoxylated derivatives of these materials being typical. Nonlimiting examples of commercially available ethoxylated materials include TWEEN® (ethoxylated sorbitan mono-, di- and/or tri-esters of C12 to C18 fatty acids with an average degree of ethoxylation of from about 2 to 20).

One type of preferred nonionic surfactants include alkoxylated alcohols such as a polyethylene derivative of hydrogenated castor oil, for example, PEG-40 hydrogenated castor oil, commercially available from the company Cognis (BASF) under the tradename Eumulgin® HRE 40 or Cremophor® CO 40.

The at least one nonionic surfactant is typically present in an amount from about 0.5 by weight to about 30% by weight, typically in an amount from about 1 by weight to about 20% by weight, more typically from about 0.5 by weight to 15% by weight, and even more typically from about 0.5 by weight to 10% by weight, or from about 0.5 to about 5% by weight, or from about 0.5 to about 2% by weight, including all ranges and subranges there-between, relative to the weight of the composition of the present invention.

Lipophilic Compounds

The compositions of the present invention can further comprise at least one lipophilic compound which can be chosen from plant oils, fatty esters, waxes, fatty acids and salts thereof, lipophilic vitamins and esters thereof, organic sunscreens, phospholipids, and mixtures thereof.

Non-limiting examples of plant oils include olive oil, avocado oil, coconut oil, safflower oil, almond oil, castor oil, jojoba oil, peanut oil, sesame oil, hazelnut oil, sunflower oil, apricot kernel oil, grapeseed oil, palm oil, argan oil, squalane and pracaxi oil.

Non-limiting examples of waxes include paraffin wax, beeswax, candelilla wax, carnauba wax, jasmine wax, jojoba wax and mimosa wax.

Suitable fatty acids include those containing from 8 to 30, preferably from 12 to 24 carbon atoms, and carboxylate salts of fatty acids. The sodium, potassium, ammonium, calcium and magnesium carboxylates of fatty acids listed are typical examples of the carboxylate salts of the fatty acids.

Non-limiting preferred fatty esters include esters formed from fatty acids and $C_1$-10 alcohols and esters formed from the fatty alcohols as defined hereabobe and $C_{1-10}$ carboxylic acids.

In addition, non-limiting specific examples of lipophilic compounds include isopropyl palmitate, capric/caprylic triglyceride, isodecyl neopentanoate, polyIsobutylene, Phloretin, Ellagic acid, Vitamin D, Vitamin E, Vitamin E Acetate, Vitamin A, Vitamin A Palmitate, 2-oleamido-1,3-octadecanediol, octyl methoxycinnamate, octyl salicylate, 18-Methyleicosanoic acid, and mixtures thereof. Other types of lipophiles include organic sunscreens, phospholipids, and other water-insoluble vitamins.

According to one embodiment, the at least one lipophilic compound is chosen from plant oils, waxes, fatty acids having at least 12 carbon atoms, fatty esters and mixtures thereof.

According to another embodiment, the at least one lipophilic compound comprises fragrance oils.

The at least one lipophilic compound is present in the composition of the present invention in an amount of from about 0.1 to about 20% by weight, such as from about 0.3 to about 10% by weight, and from about 0.5 to about 5% by weight, including all ranges and subranges there-between, relative to the total weight of the composition.

As skin and hair active agents that may be used in the composition of the present invention, examples that may be mentioned include moisturizers, for example, protein hydrolysates and sugar derivatives; natural and plant extracts; anti-inflammatory agents; antioxidants; anti-wrinkle agents; procyannidol oligomers; vitamins, for instance vitamin A (retinol), vitamin C (ascorbic acid), vitamin E (tocopherol), vitamin B5 (panthenol), vitamin B3 (niacinamide), derivatives of these vitamins (especially esters) and mixtures thereof; urea; caffeine; depigmenting agents such as kojic acid, hydroquinone and caffeic acid; salicylic acid and its derivatives; α-hydroxy acids such as lactic acid and glycolic acid and derivatives thereof; β-hydroxy acids, α-keto acids, β-keto acids, retinoids such as carotenoids and vitamin A derivatives; sunscreens; self-tanning agents; hydrocortisone; melatonin; algal, fungal, plant, yeast or bacterial extracts; enzymes; DHEA and its derivatives and metabolites; antibacterial active agents, for instance 2,4,4'-trichloro-2'-hydroxydi-phenyl ether (or Triclosan), 3,4,4'-trichloro-carbanilide (or Triclocarban); mattifying agents and mixtures thereof.

Non-limiting examples of sunscreens include benzophenones, bornelone, butyl PABA, cinnamidopropyl trimethyl ammonium chloride, disodium distryrylbiphenyl disulfonate, PABA, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, ethylhexyl dimethyl PABA, red petrolatum, and mixtures thereof.

Non-limiting examples of preservatives include polyvinyl alcohol, phenoxyethanol, benzyl alcohol, methyl paraben, propyl paraben and mixtures thereof.

Non-limiting examples of pH adjusting agents include potassium acetate, sodium carbonate, sodium hydroxide, phosphoric acid, succinic acid, sodium citrate, citric acid, boric acid, lactic acid, sodium hydrogen carbonate and mixtures thereof.

Yet other examples of auxiliary ingredients that may be present in the inventive compositions include fragrances, preservatives, colorants, glitter, fillers/powders, buffers, chelators (such as EDTA and salts thereof, particularly sodium and potassium salts), reducing agents, plasticizers, softeners, antifoaming agents, inorganic colloids, peptizing agents, pearlescent agents, penetrants, opacifying agents, and any other additive or adjuvant conventionally used in cosmetic compositions intended to be applied to the hair. The compositions may further contain polymers other than the silicone-organic polymer hybrid compound of the invention, provided that they are compatible with the other ingredients therein.

The at least one auxiliary ingredient is present in the composition in a preferred amount of from about 0.001 to about 50% and more preferably from about 0.01 to about 20% by weight, including all ranges and subranges therebetween, relative to the weight of the composition.

One embodiment of the present invention is a hair cosmetic composition comprising, in a cosmetically acceptable carrier, at least two latex polymers comprising acrylates copolymer and polyurethane-34, and from about 2% to about 4% by weight, relative to the weight of the composition, of at least one silicone-organic polymer compound selected from Crotonic Acid/Vinyl C8-12 Isoalkyl Esters/VA/Bis-Vinyldimethicone Crosspolymer;
  wherein the at least two latex polymers are film-forming polymers;
  wherein the at least two latex polymers are present in a combined amount ranging from about 0.45 to about 2.21% by weight, relative to the weight of the composition; and
  wherein the at least two latex polymers are present in the composition in a weight ratio ranging from about 3:1 to about 1:3.

In one embodiment, the composition of the present invention is a composition for styling hair and/or maintaining the style of hair.

In other embodiments, the composition of the present invention additionally contains a volatile organic solvent/compound.

In one preferred embodiment the composition of the present invention is in the form of a spray composition.

In other embodiments the composition of the present invention contains a propellant.

In yet other embodiments the composition of the present invention does not contain a propellant.

In some embodiments, the composition of the present invention is in the form of a non-aerosol spray, such as a pump spray, preferably containing a volatile organic solvent/compound. In some embodiments, when the composition of the present invention is in the form of a pump spray, the pump spray device is not an aerosol device. In some other embodiments, when the composition of the present invention is in the form of a pump spray, the composition does not contain a propellant.

The compositions of the present invention can be formulated and applied onto hair as a spray, such as a pump spray or such as a non-aerosolized spray, even when the compositions have a low content of volatile organic solvent such as ethanol, i.e., the composition does not contain more than about 10% by weight, or not more than about 6% by weight, or not more than about 5% by weight, or not more than about 4% by weight of at least one volatile organic solvent, relative to the total weight of the composition.

In other embodiments, the composition of the present invention is in the form of a non-spray product such as a cream, lotion, wax, paste, and gel.

In one embodiment, the composition of the present invention does not contain an anionic polymer other than the silicone-organic polymer compound of the present invention.

Method of Making

The hair cosmetic composition of the invention is made by:

A. combining, in a cosmetically acceptable carrier, at least two latex polymers selected from acrylate latex polymers and polyurethane latex polymers and at least one silicone-organic polymer compound;

wherein at least one latex polymer is a film-forming polymer;

wherein the at least two latex polymers are selected from:
  (a) polymer A, having a Young's modulus ranging from about 0.1 MPa to about 10 MPa and a strain, under stress at 0.5 MPa, of at least about 1%;
  (b) polymer B, having a Young's modulus ranging from about 10 MPa to about 6 GPa and a strain, under stress at 0.5 MPa, of less than about 5%; and
  (c) polymer C, selected from non-film-forming latex polymers;

wherein the at least two latex polymers are present in a combined amount ranging from about 0.25% to about 3.5% by weight, relative to the weight of the composition; wherein the at least one silicone-organic polymer compound is present in a total amount ranging from about 0.5% to about 10% by weight, relative to the weight of the composition; and wherein the at least two latex polymers are present in the composition in a weight ratio ranging from about 10:1 to about 1:10; and B. mixing the ingredients in A in order to form the hair cosmetic composition.

A neutralizing agent may be employed in the above-described method in an amount sufficient to fully or partially neutralize, depending on the desired degree of neutralization, the at least one silicone-organic polymer compound.

In an embodiment, the at least one silicone-organic polymer compound is first combined with an amount of a neutralizing agent sufficient to fully or partially neutralize (as desired) the silicone-organic polymer compound. The fully or partially neutralized silicone-organic polymer compound is then combined and mixed with one or more of the rest of the ingredients of the hair cosmetic composition of the invention.

Method of Use

The method or process of using the compositions of the present invention may depend on the type of hair being targeted and, consequently, on the specific ingredients contained in the composition used to style of shape the hair.

An embodiment of the present invention is a method of styling hair.

Another embodiment of the present invention is a method of imparting durable or long-lasting frizz control to hair comprising applying onto the hair, any one of the compositions of the present invention.

Another embodiment of the present invention is a method of controlling frizziness of hair comprising applying onto the hair, any one of the compositions of the present invention.

According to at least one embodiment, such a method comprises applying to the hair, an effective amount of any one of the compositions of the present invention.

The compositions of the present invention may be employed in an effective amount to adequately cover the surface of the fibers of the hair and to achieve a desirable or effective style or shape of the hair as well as a desirable degree of hold. The precise amount of composition to be applied onto the hair will thus depend on the degree of treatment/styling/shaping/hold desired.

An effective amount of the composition is typically from about 0.1 gram to about 50 grams, preferably from about 0.5 gram to about 20 grams of the composition. Application to the hair typically includes working the composition through the hair.

Further disclosed herein is the use of the compositions of the present invention for shaping or styling hair and/or retaining a hairstyle.

The compositions may be applied to wet or dry hair, before or after shaping. They may be used in a non-rinse fashion in order to impart or maintain the shape of the hair. In some other embodiments, the composition may be rinsed from the hair.

One embodiment of the present invention is a method of imparting durable or long-lasting frizz control comprising contacting hair with the compositions of the invention, heating the hair and optionally, applying a smoothing action to the hair while heating the hair or after heating the hair.

The hair that has been contacted with the compositions of the present invention may be air-dried and/or further styled or shaped by applying heat on the hair using a blow dryer, hood dryer or hair dryer, flat iron, heating implement, or other suitable devices, such as a hot iron or curling iron, and/or by combing or brushing or running the fingers through the hair. Other shaping tools may be chosen from combs and brushes.

In certain embodiments, the composition is allowed to remain (leave-on time) on the keratin fibers, for example, from about 1 to about 60 minutes, or such as from about 5 to about 45 minutes, or such as from about 5 to about 30 minutes, or such as from about 10 to about 20 minutes, or such as at about 20 minutes, or such as at about 10 minutes.

The smoothing action may be accomplished by use of suitable devices for brushing or smoothing the hair include a hair brush, comb, or flat iron. The smoothing action on the hair may also include running the fingers through the hair.

A suitable applicator device is an applicator brush.

Heat (at a temperature of at least 40° C.) can be applied to the hair while the smoothing action is performed on the hair. The heat source can be chosen from a blow dryer, a flat iron, a hair dryer, a heat lamp, a heat wand, or other similar devices.

In addition, independently of the embodiment use, the composition present on the fibers or hair is left in place for a time, generally, from about 1 to about 60 minutes, such as from about 5 to about 45 minutes, or such as from about 5 to about 20 minutes, or such as from about 10 to about 20 minutes, or such as of about 20 minutes or such as of about 10 minutes.

It was surprisingly and unexpectedly discovered that the application of the composition onto the hair results in satisfactorily controlling the frizziness of hair.

The frizz control effects obtained using the compositions and methods of the present invention may also be durable, i.e., wash or shampoo resistant.

The compositions of the present invention may be packaged in any suitable container such as a tube, a jar or a bottle. In certain embodiments, the composition can be packaged in a tube or bottle, for example, a squeeze tube or squeeze bottle.

Additionally, the applicator device can be attached or connected to the opening of the packaging tube or bottle wherein the applicator device is a brush or a comb with teeth such that the ends of the teeth have openings from which the composition of the invention can flow through and be applied directly onto the hair. As used herein, the process and composition disclosed herein may be used on the hair that has not been artificially dyed, pigmented or permed.

Another embodiment of the present invention is a method for imparting durable or long-lasting frizz control to hair comprising (a) providing the composition of the present invention, and (b) providing instructions for applying said composition to the hair.

Instructions for applying the composition of the present invention onto keratin fibers such as hair on the head or eyelashes may comprise directions of use of the composition for the end-user to follow. The end-user may be a consumer or cosmetologist or salon hair dresser. Directions may comprise instructing the end-user to take an amount of the composition in sufficient quantity such that the composition adequately covers the hair fibers and imparts the desired shape or style or hold to the hair fibers. Directions may additionally instruct the end-user to use a device such as a comb, brush (e.g., hair brush or brush wand), flat iron plates, blow dryer or the fingers for shaping or styling the hair or for separating the fibers of the hair. Directions may also additionally instruct the end-user to apply heat to the hair such as by blow drying the hair or using a heating device on the hair.

Instructions for applying the composition of the present invention onto keratin fibers such as hair may appear on the container (such as can, bottle or jar) holding the composition of the present invention or on the box or carton or other packaging comprising the container holding said composition.

It has been surprisingly and unexpectedly discovered that the combination of at least two latex polymers, at least one silicone-organic polymer compound, and a cosmetically acceptable carrier produced a composition that resulted in satisfactory styling or shaping of hair, including long lasting or durable style or wear on the hair, very good and durable/long lasting frizz control benefits, even when the hair contacted with the composition was exposed to high humidity conditions or subjected to multiple cycles of shampooing and/or washing with water.

The degree of styling or shaping hold on the hair may be evaluated by assessing the appearance of the hair, or quantitatively assessing the degree of frizziness or reduction in frizziness of the hair, or the retention of curl elongation or straightness of the hair after contacting the hair with the composition of the invention. The assessments can be continuously made over time, or with exposure to high humidity conditions or with multiple cycles of shampooing and/or washing with water.

As used herein, the method and composition disclosed herein may be used on the hair that has not been artificially dyed, pigmented or permed or on the hair that has been artificially dyed, pigmented or permed.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result.

EXAMPLES

The following Examples are intended to be non-restrictive and explanatory only, with the scope of the invention being defined by the claims.

The ingredient amounts/concentrations in the compositions/formulas described below are expressed in % by weight, based on the total weight of the composition/formula.

Procedure for Determination of Physical Properties of Latex Films

Film Plating:

The latex film was obtained by allowing a 30 gram water solution containing 4 grams of the latex polymer(s) to dry slowly in a 100 mL PFA Petri dish (100 mm diameter×15 mm height) at room temperature for at least 3 days.

Film Measurement:

The latex film, with known dimensions (length, width, thickness), was mounted on the Q800 Dynamic Mechanical Analysis from TA Instrument, and tested in a DMA Control Force mode. The stress/strain test was obtained using the following procedure:
Preload force: 0.001 N
Isothermal: 25° C.
Soak time: 0.5 minutes
Force ramp rate: 0.5 N/min to 18 N The test ended when the sample broke, 18 N force was reached, or maximum displacement was achieved (25.5 mm).

From the stress/strain curve, the Young's Modulus was calculated as the slope of the linear portion at about 0.01% Strain to about 1% Strain. From the stress/strain curve, the % Strain at the stress of 0.5 MPa was also reported.

A high Young's Modulus demonstrates a hard film, while a lower Young's Modulus represents a more elastic film. A high Strain demonstrates a stretchy, elastic film, while a lower Strain represents a more brittle film.

Film properties of latex polymers as measured according to the above-described "Procedure for Determination of Physical Properties of Latex Films":
Acrylates copolymer, commercially available from BASF in an aqueous dispersion under the trade name of LUVIFLEX SOFT=Young's Modulus of 2758 MPa and strain, under stress at 0.5 MPa, of <0.01%.
Polyurethane-34, commercially available from BAYER in an aqueous dispersion under the trade name of BAYCUSAN C1001=Young's Modulus of 3 MPa and strain, under stress at 0.5 MPa, of 18.82%.

Example 1

Formulas (Inventive and Comparative)

| Phase | INCI Name | Formula A Inventive | Formula B Latex only (acrylates* and PU-34**) | Formula B P1101*** only Comparative | Formula C Comparative Silicone**** | Formula D Latex + comparative silicone |
|---|---|---|---|---|---|---|
| | | | | % wt/wt | | |
| A1 | DI WATER | 88.778 | 92.881 | 95.897 | 98.000 | 88.778 |
| 2 | ACRYLATES COPOLYMER (27%) DISPERSION IN WATER LUVIFLEX SOFT (BASF) | 5.556 | 5.556 | — | — | 5.556 |
| 3 | POLYURETHANE-34 (32%) DISPERSION IN WATER BAYCUSAN C 1001 | 1.563 | 1.563 | — | — | 1.563 |
| B1 | CROTONIC ACID/VINYL C8-12 ISOALKYL ESTERS/VA/BIS-VINYLDIMETHICONE CROSSPOLYMER (50%) IN ALCOHOL BELSIL P1101 (WACKER) | 4.000 | — | 4.000 | — | — |
| 2 | AMINOETHYL PROPANOL ANGUS (DOW CHEMICAL) | 0.103 | — | 0.103 | — | — |
| 2 | PEG/PPG-17/18 DIMETHICONE XIAMETER OF X-5220 FLUID (DOW CORNING) | — | — | — | 2.000 | 2.000 |

Example 2

Inventive Formulas (Varying Amounts of Latex Polymers (Total Amount) and P1101)

| Phase | Chemical Name | Formula 1 (2, 2)* % wt | Formula 2 (2, 4)* % wt | Formula 3 (1, 4)* % wt | Formula 4 (1, 2)* % wt |
|---|---|---|---|---|---|
| A1 | DI WATER (QS) | 82.579 | 80.475 | 84.034 | 84.034 |
| A2 | PHENOXYETHANOL (SEPPIC) | 0.900 | 0.900 | 0.900 | 0.900 |
| A3 | ETHYLHEXYLGLYCERIN | 0.100 | 0.100 | 0.100 | 0.100 |
| A4 | ACRYLATES COPOLYMER (27%) DISPERSION IN WATER** LUVIFLEX SOFT (BASF) | 5.556 | 5.556 | 2.778 | 2.778 |
| A5 | POLYURETHANE-34 (32%) DISPERSION IN WATER BAYCUSAN C 1001 | 1.563 | 1.563 | 0.781 | 0.781 |
| B1 | CROTONIC ACID/VINYL C8-12 ISOALKYL ESTERS/VA/BIS-VINYLDIMETHICONE CROSSPOLYMER (50%) IN ALCOHOL BELSIL P1101 (WACKER) | 4.000 | 8.000 | 8.000 | 4.000 |
| B2 | AMINOMETHYL PROPANOL [ANGUS (DOW CHEMICAL)] | 0.103 | 0.207 | 0.207 | 0.103 |
| B3 | DENATURED ALCOHOL | 4.000 | 2.000 | 2.000 | 4.000 |
| C1 | PEG-40 HYDROGENATED CASTOR OIL | 0.800 | 0.800 | 0.800 | 0.800 |
| C2 | FRAGRANCE | 0.400 | 0.400 | 0.400 | 0.400 |

*% by weight in total of active acrylates copolymer and PU-34, % by weight of active P1101; % weights based on the weight of the formula Process of Making the Inventive Formulas:

The formulas above consist of three phases; A, B, and C. In phase A, all raw materials were added separately and mixed until uniform. In phase B (separate beaker), the respective raw materials were mixed until the solution was uniform, indicating that P1101 is neutralized to 100%. This phase was then added to the main tank. In phase C (separate beaker), Peg-40 Hydrogenated castor oil was first melted at 40-45° C., and followed by the addition of the fragrance. Once the raw materials were mixed until uniformity was achieved, this phase was then added to the main tank. The raw materials were added in order of representation on the respective charts. Rayneri mixers were used to batch all of the formulations.

Note: P1101 was neutralized to 100%, based on the acid value of the lot number of the resin, in all formulas.

Example 3

Testing for Shampoo/Wash-Resistant Frizz Control and Shampoo/Wash-Resistant Curl Elongation A. The formulas in Example 1 above were tested on curly/frizzy hair swatches.

Test Procedure using width (frizz control) measurements on swatches:
1. Hair swatches, 1.4+/−0.10 g each of curly/frizzy were prepared; 2 per treatment=6 total
2. Wash hair tresses with RDK Cleansing Cream by thoroughly wetting each swatch, applying 1.5 g of shampoo to hair, spreading it along the hair until saturation, then washing it off under running water.
3. Air dry swatches overnight. First measurement of width is taken (T0).
4. Treated swatches were treated by spraying 1 g of product (or water as the control) onto the tress and combing it through 3 times then flat-ironed at 1"/sec, 450 F, 3 passes each. Untreated swatches were treated by combing 3 times and flat-ironed at 1"/sec, 450 F, 3 passes each. Second measurement of width is taken (T1).
5. Swatches were left overnight. Third measurement of width is taken (T2).
6. Swatches were washed with a cleansing composition following the procedure in (2) and laid out to air-dry overnight.
7. Fourth measurement of width is taken (T3). Undisturbed dry swatches width was measured.
8. Swatches were then brushed 3 passes each and measurement of width is taken again. Fifth measurement of width is taken (T4).

Width measurements on hair swatches at different time periods, Example 1 formulas

TABLE A

| | | Average % change** | | | | |
|---|---|---|---|---|---|---|
| Formula | (T0) | (after treatment) | (after 8 hrs) | (after 1 wash) | (after 2 washes) | (after 3 washes) |
| DI Water | 0.00 | −43.98 | 14.90 | 18.26 | 57.66 | 51.52 |
| A (Latex + P1101) | 0.00 | −63.85 | −42.87 | −31.57 | −34.88 | −18.11 |
| B (Latex) | 0.00 | −59.73 | −24.75 | −33.58 | −4.87 | 13.02 |
| C (P1101) | 0.00 | −56.40 | −8.74 | −18.70 | 7.87 | −0.36 |
| D (Silicone) | 0.00 | −64.83 | −30.23 | −4.11 | 42.60 | 44.82 |
| E (Latex + Silicone) | 0.00 | −59.08 | −33.08 | −20.58 | 15.85 | 24.03 |

**Average % change is based on the % width changes calculated per swatch; % width change is calculated from the difference between the initial or starting measurement (T0) minus the measurement at a time period (e.g., after treatment) divided by the initial measurement and then multiplied by 100.

TABLE B

| Formula | | | stdev | | | |
| --- | --- | --- | --- | --- | --- | --- |
| DI Water | 0.00 | 0.40 | 7.64 | 6.31 | 6.71 | 13.96 |
| A (Latex + P1101) | 0.00 | 7.76 | 4.70 | 6.74 | 9.42 | 5.32 |
| B (Latex) | 0.00 | 7.84 | 5.98 | 10.13 | 9.72 | 19.88 |
| C (P1101) | 0.00 | 10.96 | 9.02 | 6.33 | 6.85 | 13.04 |
| D (Silicone) | 0.00 | 9.19 | 17.61 | 8.31 | 20.49 | 4.86 |
| E (Latex + Silicone) | 0.00 | 2.49 | 3.85 | 9.13 | 15.84 | 11.75 |

The comparative study results above show that all the test products or formulas provided some degree of durable or longer lasting style compared to the control (water) treatment, 8 hours after treatment at 90% humidity and after the first wash cycle (T1). However, after the second wash cycle (T2) and the third wash cycle (T3), only the inventive formula retained most of its width reduction capability, thus showing long-term or longer lasting styling benefits (shampoo/wash-resistant style or shape) which can be attributed to the deposition of a shampoo/wash-resistant film produced by the inventive formula on the hair.

B. The formulas in Example 2 above were tested on curly/frizzy hair swatches subjected to 10 wash cycles. Half of the treated swatches were also subjected to heat (by flat iron).

Test Procedure using width (frizz control) and length (curl elongation) measurements on swatches:

1. Hair swatches, 1.5+/−0.10 g each of curly/frizzy were prepared; 2 swatches for each treatment and 1 swatch for 511 S controls (18 swatches total).
2. Wash hair tresses with RDK Cleansing Cream by thoroughly wetting each swatch, applying 1 g of shampoo to hair, spreading it along the hair swatch and massage from top to bottom 10 times, then washing it off under running water.
3. Air dry overnight in humidity chamber at controlled humidity (RH 80%). Comb through 3 times for each tress. Measure the width/Length (T0). Width is measured at the ends, including fly-aways.
4. Apply 0.5 g of product onto each tress, comb it through 3 times and let saturate for 3 minutes.
5. For heat treatment: flat-iron at r/sec, at 450 F, 3 passes each. For no-heat treatment (air dry): proceed to next step.
6. Measurement of width/length is taken (T1).
7. Swatches are placed in humidity chamber (80% RH) for 8 hrs. Measurement of width/length is taken (T2).
8. Swatches are washed with a cleansing composition and left to air dry overnight at controlled humidity (RH 80%). Dried tresses are combed through 3 times each and measurement of width/length is taken (T3).
9. Repeat procedure in Step 8 and measure width/length. Continue to repeat procedure in Step 8 and measure width/length for 10 washes total.

Width and length measurements on hair swatches at different time periods (hair treated with Example 2 formulas; two swatches per treatment)*

TABLE 1

WIDTH MEASUREMENTS (AVERAGE % CHANGE),** WITH HEAT

| Formula | T0 | T1 | T2 | T3 | T4 | T5 | T6 | T7 | T8 | T9 | T10 | T11 | T12 |
| --- | --- | --- | --- | --- | --- | --- | --- | --- | --- | --- | --- | --- | --- |
| water | 0 | −61 | −43 | −7.1 | −7.1 | −7.1 | −7.1 | −7.1 | −7.1 | −7.1 | −7.1 | −7.14 | −7.14 |
| 1 (1, 2) | 0 | −76 | −76 | −50 | −48 | −46 | −39 | −33 | −26 | −20 | −18 | −14.7 | −9.07 |
| 2 (1, 4) | 0 | −80 | −78 | −60 | −52 | −52 | −40 | −40 | −40 | −40 | −32 | −23.7 | −19.9 |
| 3 (2, 2) | 0 | −84 | −76 | −66 | −64 | −59 | −56 | −56 | −47 | −35 | −29 | −25.2 | −21.3 |
| 4 (2, 4) | 0 | −86 | −86 | −74 | −66 | −58 | −59 | −63 | −57 | −51 | −49 | −47.2 | −47.2 |

**Average % change is based on the % width or length changes calculated per swatch; % width or length change is calculated from the difference between the initial or starting measurement (T0) minus the measurement at a time period (e.g., T1) divided by the initial measurement and then multiplied by 100

TABLE 2

WIDTH MEASUREMENTS (AVERAGE % CHANGE), NO HEAT

| Formula | T0 | T1 | T2 | T3 | T4 | T5 | T6 | T7 | T8 | T9 | T10 | T11 | T12 |
| --- | --- | --- | --- | --- | --- | --- | --- | --- | --- | --- | --- | --- | --- |
| water | 0 | −77 | −38 | −15 | −15 | −12 | −7.7 | −3.8 | −3.8 | −7.7 | 0 | 0 | 0 |
| 1 (1, 2) | 0 | −93 | −93 | −61 | −50 | −48 | −46 | −41 | −33 | −22 | −20 | −18.4 | −18.4 |
| 2 (1, 4) | 0 | −94 | −94 | −69 | −60 | −61 | −47 | −49 | −43 | −34 | −30 | −30.4 | −26.5 |
| 3 (2, 2) | 0 | −95 | −95 | −71 | −75 | −66 | −60 | −60 | −58 | −27 | −24 | −24.5 | −20.3 |
| 4 (2, 4) | 0 | −96 | −95 | −79 | −69 | −69 | −69 | −69 | −69 | −62 | −62 | −61.5 | −61.5 |

TABLE 3

LENGTH MEASUREMENTS (AVERAGE % CHANGE), WITH HEAT

| Formula | T0 | T1 | T2 | T3 | T4 | T5 | T6 | T7 | T8 | T9 | T10 | T11 | T12 |
| --- | --- | --- | --- | --- | --- | --- | --- | --- | --- | --- | --- | --- | --- |
| water | 0 | 18.8 | 12.5 | 0 | 3.13 | 0 | 0 | 0 | 0 | 0 | 0 | 0 | 0 |
| 1 (1, 2) | 0 | 23.8 | 23.8 | 9.53 | 1.61 | 1.61 | 7.96 | 4.79 | 1.61 | 1.61 | 1.61 | 1.613 | 1.613 |
| 2 (1, 4) | 0 | 24.6 | 24.6 | 11.5 | 9.84 | 8.23 | 4.95 | 4.95 | 4.95 | 4.95 | 4.95 | 4.946 | 4.946 |
| 3 (2, 2) | 0 | 21.9 | 23.5 | 16.8 | 8.4 | 6.67 | 4.95 | 4.95 | 5.06 | 5.06 | 5.06 | 3.448 | 3.448 |
| 4 (2, 4) | 0 | 22.7 | 22.7 | 13 | 11.4 | 8.13 | 8.13 | 4.9 | 3.33 | 0.1 | 0.1 | 6.563 | 6.563 |

TABLE 4

LENGTH MEASUREMENTS (AVERAGE % CHANGE); ; WITHOUT HEAT

| Formula | T0 | T1 | T2 | T3 | T4 | T5 | T6 | T7 | T8 | T9 | T10 | T11 | T12 |
|---|---|---|---|---|---|---|---|---|---|---|---|---|---|
| water | 0 | 15.6 | 0 | 0 | 0 | 0 | 0 | 0 | 0 | 0 | 0 | 0 | 0 |
| 1 (1, 2) | 0 | 14.1 | 14.1 | 6.25 | 3.13 | 1.56 | 0 | 0 | 0 | 0 | 0 | 0 | 0 |
| 2 (1, 4) | 0 | 14.1 | 14.1 | 9.38 | 1.56 | 1.56 | 1.56 | 0 | 0 | 0 | 0 | 0 | 0 |
| 3 (2, 2) | 0 | 17 | 17 | 13.6 | 10.2 | 10.2 | 1.72 | 1.72 | 5.11 | 3.39 | 3.39 | 3.391 | 3.391 |
| 4 (2, 4) | 0 | 18.3 | 18.3 | 16.7 | 6.67 | 8.33 | 6.67 | 6.67 | 6.67 | 3.33 | 3.33 | 0 | 0 | standard deviation on the measurements ranged from 0 to 2.12

Average % change is based on the % width or length changes calculated per swatch; % width or length change is calculated from the difference between the initial or starting measurement (T0) minus the measurement at a time period (e.g., T1) divided by the initial measurement and then multiplied by 100 Time periods: T0=initial, T1=after treatment, T2=after 8 hours in 80% relative humidity, T3=after 1 wash, T4=after 2 washes, T5=after 3 washes, T6=after 4 washes, T7=after 5 washes, T8=after 6 washes, T9=after 7 washes, T10=after 8 washes, T10=after 9 washes, T11=after 10 washes Overall, the swatches treated with the inventive formulas exhibited shampoo/wash resistant style or shape for at least 3 washes at a width reduction of at least 45%. Furthermore, formula 2 with higher concentrations of P1101 and latex polymers (2% and 4%, respectively), exhibited the greatest effect of long-lasting style or shape and shampoo/wash-resistant style or shape, at width reductions of greater than 60% after 5 washes and greater than 45% after 10 washes. It was found that the width reduction was more pronounced for heat-untreated swatches compared to those that were heat-treated (use of flat iron) signifying that heat application did not significantly influence wash resistance.

For the curl elongation (length) measurements, the results show that the % of length increase exhibited by the swatches (heated and not heated) treated by the inventive formulas remained comparable after 8 hours post-treatment at 80% humidity. In general, greater curl elongation effects were evident for the swatches treated with the formulas that contained the higher amounts of latex polymers and P1101.

It was noted that the effect and long lastingness of width reduction (frizz control) was more significant than that of length changes or curl elongation effects: swatches returned to their original length (+/−10%) within two to three washes, while width reduction was retained for significantly longer periods of time or over a greater number of wash cycles (five to ten wash cycles). This finding suggests that the association of two latex polymers and P1101 results in hair frizz control through fiber alignment without distortion of the disulfide bonds within the keratin fibers.

The foregoing description illustrates and describes the present invention. Additionally, the disclosure shows and describes only the preferred embodiments of the invention, but, as mentioned above, it is to be understood that it is capable of changes or modifications within the scope of the concept as expressed herein, commensurate with the above teachings and/or skill or knowledge of the relevant art. The embodiments described hereinabove are further intended to explain best modes known of practicing the invention and to enable others skilled in the art to utilize the disclosure in such, or other, embodiments and with the various modification required by the particular applications or uses disclosed herein. Accordingly, the description is not intended to limit the invention to the form disclosed herein. Also, it is intended that the appended claims be construed to include alternative embodiments.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

What is claimed is:

1. A hair cosmetic composition comprising, in a cosmetically acceptable carrier,
    (a) (1) latex polymer A having a Young's modulus ranging from about 0.1 Mpa to about 10 MPa, and a strain, under stress at 0.5 MPa, of at least about 1%, wherein latex polymer A is Acrylates copolymer, Acrylates/Ethylhexyl Acrylate copolymer, Acrylates/VA copolymer, Polyurethane-34, Polyurethane-32, or Polyurethane-48; and
    (2) latex polymer B having a Young's modulus ranging from about 10 MPa to about 6 GPa, and a strain, under stress at 0.5 MPa, of less than about 5%, wherein latex polymer B is Acrylates copolymer, Polvacrylate-2 crosspolymer, Styrene/Acrylic copolymer, Polyurethane-35, Polyurethane-1, Polycarbamyl Polyqlycol Ester, Styrene/Acrylates Copolymer, or Styrene/Acrylates/Ammonium Methacrylate Copolymer;
    wherein latex polymers A and B are dispersed particles in an aqueous dispersion medium; and
    (b) Crotonic Acid/Vinyl C8-12 Isoalkyl Esters/VA/Bis-Vinyldimethicone Crosspolvmer;
    where latex polymers A and B are present in a combined amount ranging from about 0.25% to about 3.5% by weight, relative to the weight of the composition;
    wherein the Crotonic Acid/Vinyl C8-12 Isoalkyl Esters/VA/Bis-Vinyldimethicone Crosspolymer is present in a total amount ranging from about 0.5% to about 10% by weight, relative to the weight of the composition; and
    wherein latex polymers A and B are present in the composition in a weight ratio ranging from about 10:1 to about 1:10.

2. The hair cosmetic composition of claim 1, wherein latex polymers A and B are present in individual amounts ranging from about 0.05% to about 3% by weight, relative to the weight of the composition.

3. The hair cosmetic composition of claim 1, the weight ratio of latex polymers A:B ranges from about 1:5 to about 5:1.

4. The hair cosmetic composition of claim 1, the weight ratio of latex polymers A:B ranges from about 1:3 to about 3:1.

5. The hair cosmetic composition of claim 1, the weight ratio of latex polymers A:B is about 0.5:1.5.

6. The hair cosmetic composition of claim 1, the weight ratio of latex polymers A:B ranges from about 0.5:1.5 to about 1:3.

7. The hair cosmetic composition of claim 1, wherein the weight ratio of the total amount of the latex polymers A and B to the amount of Crotonic Acid/Vinyl C8-12 Isoalkyl Esters/VA/Bis-Vinyldimethicone Crosspolymer ranges from about 1 to about 0.25.

8. The hair cosmetic composition of claim 1, wherein polymer A is polyurethane-34 and polymer B is acrylates copolymer.

9. The hair cosmetic composition of claim 8, wherein the weight ratio of acrylates copolymer to polyurethane-34 is 3:1.

10. The hair cosmetic composition of claim 8, wherein the weight ratio of acrylates copolymer to polyurethane-34 is 1:1.

11. The hair cosmetic composition of claim 1, wherein the cosmetically acceptable carrier is selected from water, at least one cosmetically acceptable solvent selected from organic solvents, and combinations thereof.

12. The hair cosmetic composition of claim 1, further comprising at least one auxiliary ingredient selected propellants, rheology modifiers, surfactants, lipohilic compounds, skin and hair active agents, sunscreens, preservatives, fragrances, pH adjusting agents, and mixtures thereof.

13. The hair cosmetic composition of claim 1, wherein the hair cosmetic composition is in the form of a spray.

14. The hair cosmetic composition of claim 1, wherein the hair cosmetic composition is a hair styling.

15. A method of imparting durable styling to hair, the method comprising applying to the hair, a composition comprising, in a cosmetically acceptable carrier, (a) (1) latex polymer A having a Young's modulus ranging from about 0.1 Mpa to about 10 MPa, and a strain, under stress at 0.5 MPa, of at least about 1%, wherein latex polymer A is Acrylates copolymer, Acrylates/Ethylhexyl Acrylate copolymer, Acrylates/VA copolymer, Polyurethane-34, Polyurethane-32, or Polyurethane-48; and (2) latex polymer B having a Young's modulus ranging from about 10 MPa to about 6 GPa, and a strain, under stress at 0.5 MPa, of less than about 5%, wherein latex polymer B is Acrylates copolymer, Polvacrylate-2 crosspolymer, Styrene/Acrylic copolymer, Polyurethane-35, Polyurethane-1, Polycarbamyl Polyqlycol Ester, Styrene/Acrylates Copolymer, or Styrene/Acrylates/Ammonium Methacrylate Copolymer;

wherein latex polymers A and B are dispersed particles in an aqueous dispersion medium; and (b) Crotonic Acid/Vinyl C8-12 Isoalkyl Esters/VA/Bis-Vinyldimethicone Crosspolvmer;

(c) wherein latex polymers A and B are present in a combined amount ranging from about 0.25% to about 3.5% by weight, relative to the weight of the composition; and wherein latex polymers A and B are present in the composition in a weight ratio ranging from about from about 1:10 to about 10:1.

16. The method according to claim 15, further comprising a step of treating the hair with heat at a temperature ranging from about 25° C. to about 250° C. before, during, or after the application of the hair cosmetic composition.

* * * * *